(12) United States Patent
Vollet

(10) Patent No.: US 9,668,921 B2
(45) Date of Patent: ***Jun. 6, 2017

(54) EAR-ENGAGING AND EYE-COVERING HEAD ASSEMBLY

(71) Applicant: Gregg Vollet, Mount Currie (CA)

(72) Inventor: Gregg Vollet, Mount Currie (CA)

( * ) Notice: Subject to any disclaimer, the term of this patent is extended or adjusted under 35 U.S.C. 154(b) by 64 days.

This patent is subject to a terminal disclaimer.

(21) Appl. No.: 14/702,939

(22) Filed: May 4, 2015

(65) Prior Publication Data

US 2016/0015566 A1    Jan. 21, 2016

Related U.S. Application Data

(63) Continuation-in-part of application No. 13/716,432, filed on Dec. 17, 2012.

(60) Provisional application No. 61/637,373, filed on Apr. 24, 2012, provisional application No. 62/151,889, filed on Apr. 23, 2015.

(30) Foreign Application Priority Data

Dec. 14, 2012   (CA) ...................................... 2798596

(51) Int. Cl.
| | | |
|---|---|---|
| *A61F 9/02* | (2006.01) | |
| *G02C 3/02* | (2006.01) | |
| *G02C 5/14* | (2006.01) | |
| *A61F 11/14* | (2006.01) | |

(52) U.S. Cl.
CPC .............. *A61F 9/029* (2013.01); *A61F 9/025* (2013.01); *A61F 9/027* (2013.01); *A61F 11/14* (2013.01); *G02C 3/02* (2013.01); *G02C 5/143* (2013.01)

(58) Field of Classification Search
CPC .......... G02C 5/143; G02C 3/02; G02C 3/006; A42B 1/24; A42B 1/247; A42B 3/16; A42B 3/166; A42B 3/18; A42B 3/185; A42B 3/163; A61F 9/029; A61F 9/025; A61F 9/027; A61F 11/14
See application file for complete search history.

(56) References Cited

U.S. PATENT DOCUMENTS

| | | | |
|---|---|---|---|
| 1,216,635 A | | 2/1917 | Washington |
| 3,798,712 A | * | 3/1974 | Bonis ................... B43K 23/001 224/181 |
| 4,069,512 A | * | 1/1978 | Palmaer ................. A42B 3/166 2/209 |

(Continued)

OTHER PUBLICATIONS

Wayback Machine archived website page of the U.S. Department of Labour from Oct. 3, 2011, and entitled "Eye Protection in the Workplace": http://web.archive.org/web/20111003231651/http://ehs.okstate.edu/training/oshaeye.htm.

(Continued)

*Primary Examiner* — Thomas K Pham
*Assistant Examiner* — Cara Rakowski
(74) *Attorney, Agent, or Firm* — Cameron IP

(57) ABSTRACT

The present invention relates to an eye-protector assembly. The assembly includes arcuate-shaped protective cover. The assembly includes an eye-covering member pivotably connected to the protective cover. The protective cover is shaped to receive the eye-covering member when the eye-covering member is pivoted towards the cover. The assembly includes a pair of connector mechanisms for selectively coupling the protective cover to a hearing protector.

11 Claims, 22 Drawing Sheets

(56) References Cited

U.S. PATENT DOCUMENTS

| | | | |
|---|---|---|---|
| 4,856,089 | A | 8/1989 | Horton |
| 5,046,192 | A | 9/1991 | Ryder |
| 5,105,475 | A | 4/1992 | Lynd et al. |
| 5,133,596 | A | 7/1992 | Korny et al. |
| 5,278,999 | A | 1/1994 | Brown et al. |
| 5,724,119 | A | 3/1998 | Leight |
| 5,926,854 | A | 7/1999 | Grilliot et al. |
| 6,481,846 | B1 | 11/2002 | Mikysa |
| 6,511,177 | B1 | 1/2003 | Hall et al. |
| 7,020,901 | B2 | 4/2006 | Brhel |
| 7,020,903 | B2 | 4/2006 | Artzberger |
| 8,096,652 | B1 | 1/2012 | Carbone |
| 2007/0154029 | A1 | 7/2007 | Werner |
| 2010/0095977 | A1 | 4/2010 | Schmitz et al. |
| 2011/0113537 | A1* | 5/2011 | Peng .............. A61F 11/14 2/423 |
| 2011/0194029 | A1 | 8/2011 | Herrmann et al. |
| 2011/0209273 | A1 | 9/2011 | Fountain et al. |

OTHER PUBLICATIONS

Written Opinion of the International Search Authority for International Patent Application No. PCT/CA2013/050300 to Vollet.

\* cited by examiner

EAR-ENGAGING AND EYE-COVERING HEAD ASSEMBLY

CROSS REFERENCE TO RELATED APPLICATION

This application is a continuation-in-part of U.S. patent application Ser. No. 13/716,432 filed in the United States Patent and Trademark Office on Dec. 17, 2012, which in turn claims the benefit of Canadian Patent Application No. 2,798, 596 filed in the Canadian Intellectual Property Office on Dec. 14, 2012, and claims the benefit of provisional application No. 61/637,373 filed in the United States Patent and Trademark Office on Apr. 24, 2012, the disclosures of which are incorporated herein by reference and priority to which is claimed.

FIELD OF THE INVENTION

The present invention relates to a head assembly. In particular, the invention relates to an ear-engaging and eye-covering head assembly.

DESCRIPTION OF THE RELATED ART

It is known to combine earmuffs with eye protectors pivotally connected thereto. See, for example, U.S. Pat. No. 5,724,119 to Leight, United States Patent Publication No. 2011/0209273 to Fountain et al., U.S. Pat. No. 7,020,903 to Artzberger, U.S. Pat. No. 7,020,901 to Brhel, U.S. Pat. No. 6,511,177 to Hall et al. and U.S. Pat. No. 5,278,999 to Brown et al.

The above-described prior art provides eye protectors that may be damaged through scratching, by being stepped on, or by objects impacting the protectors when the head assemblies are not in use.

U.S. Pat. No. 5,105,475 to Lynd et al. discloses visor-type headgear that includes an eye-shield, a forehead section, and a detent mechanism for positioning the eye-shield within the forehead section.

The above headgear does not appear to provide a means for protecting a wearer's ears and appears to require a visor.

There is accordingly a need for an improved ear-engaging and eye-covering head assembly that is compact and robust and which may overcome the above disadvantages.

BRIEF SUMMARY OF INVENTION

The present invention provides an improved ear-engaging and eye-covering head assembly.

According to one aspect, there is provided an eye-protector assembly. The assembly includes arcuate-shaped protective cover. The assembly includes an eye-covering member pivotably connected to the protective cover. The protective cover is shaped to receive the eye-covering member when the eye-covering member is pivoted towards the cover. The assembly includes a pair of connector mechanisms for selectively coupling the protective cover to a hearing protector.

According to another aspect, there is provided a protective cover for protecting glasses when not in use. The protective cover includes spaced-apart lower ends to which frame portions of the glasses may pivotally connect. The protective cover includes an arcuate-shaped receptacle spaced-apart from the lower ends of the protective cover and within which lens-portions of the glasses may be selectively received. The protective cover includes at least one inwardly-extending protrusion shaped to selectively couple to headband portions of the hearing protector.

According to a further aspect, there is provided a protective cover for protecting glasses when not in use. The protective cover is connectable to a headband of a hearing protector. The headband is made of a pair of arcuate-shaped elongate members. The protective cover includes spaced-apart lower ends to which frame portions of the glasses may pivotally connect. The protective cover includes an arcuate-shaped receptacle spaced-apart from the lower ends of the protective cover and within which lens-portions of the glasses may be selectively received. The protective cover includes a pair of inwardly-extending channels positioned adjacent to the lower ends of the cover. Each of the channels has a pair of spaced-apart slots extending therethrough and a pair of tabs extending into respective ones of the slots. The elongate members of the headband of the hearing protector are received within the slots and extend tightly about the tabs.

BRIEF DESCRIPTION OF DRAWINGS

The invention will be more readily understood from the following description of preferred embodiments thereof given, by way of example only, with reference to the accompanying drawings, in which.

DESCRIPTION OF THE PREFERRED EMBODIMENTS

Figure 1:
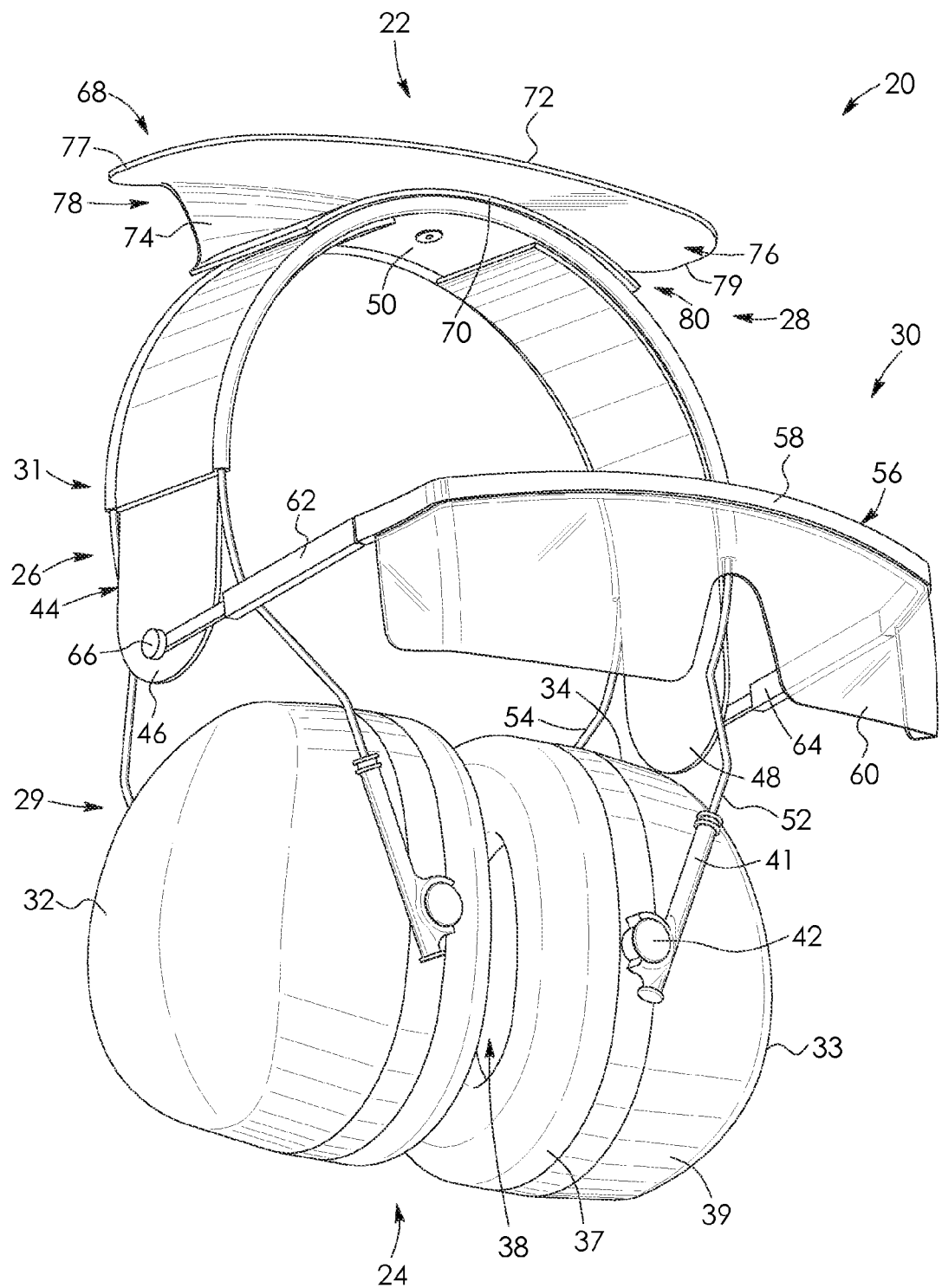
FIG. 1 is a side, front perspective view of an ear-engaging and eye-covering head assembly according to a first aspect, the assembly including a protective cover and including an eye protector shown in a lowered, first position.
Figure 3:
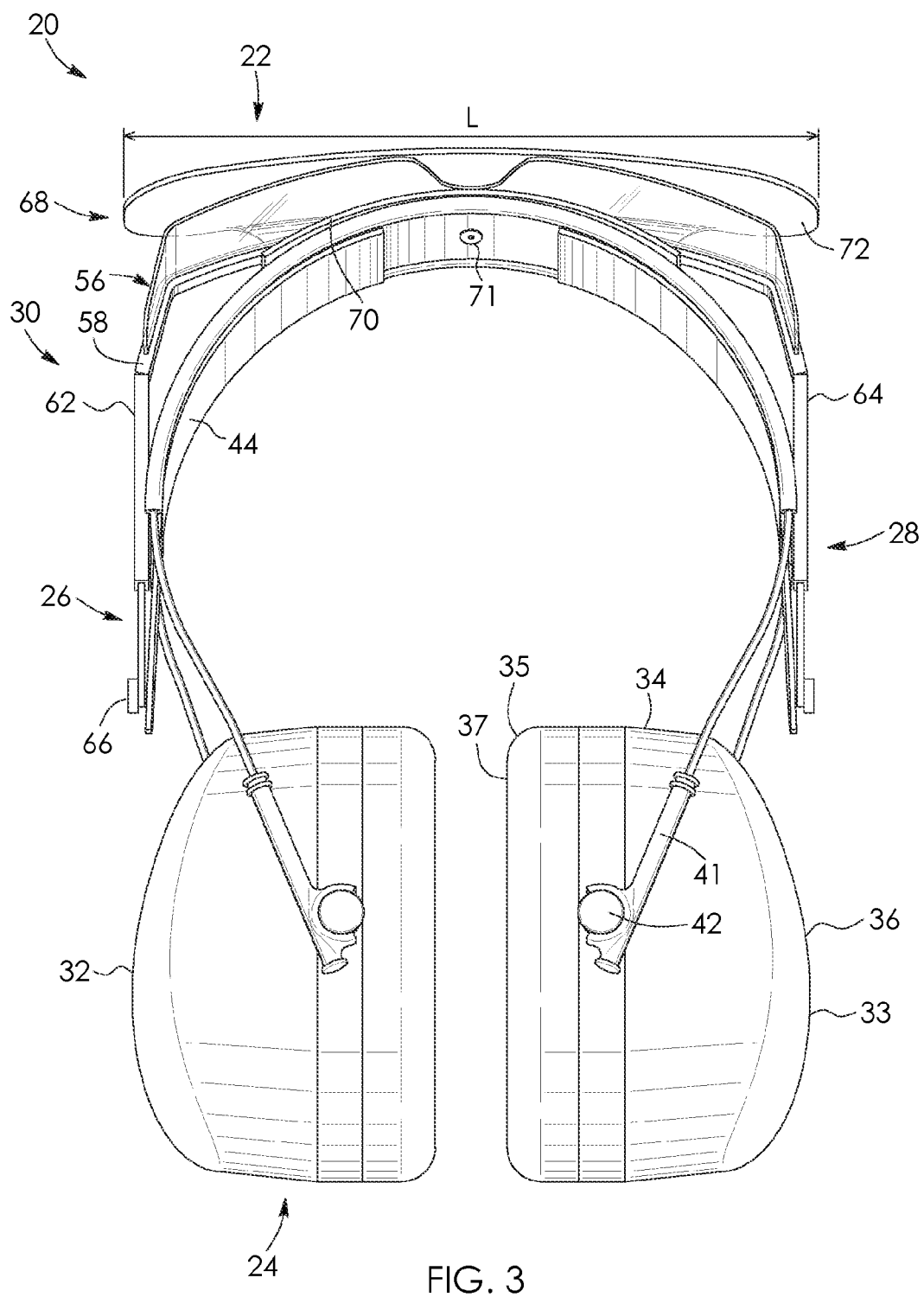
FIG. 3 is a front elevation view of the assembly shown in FIG. 1, the eye protector being positioned in a raised, second position within the protective cover.
Figure 5:
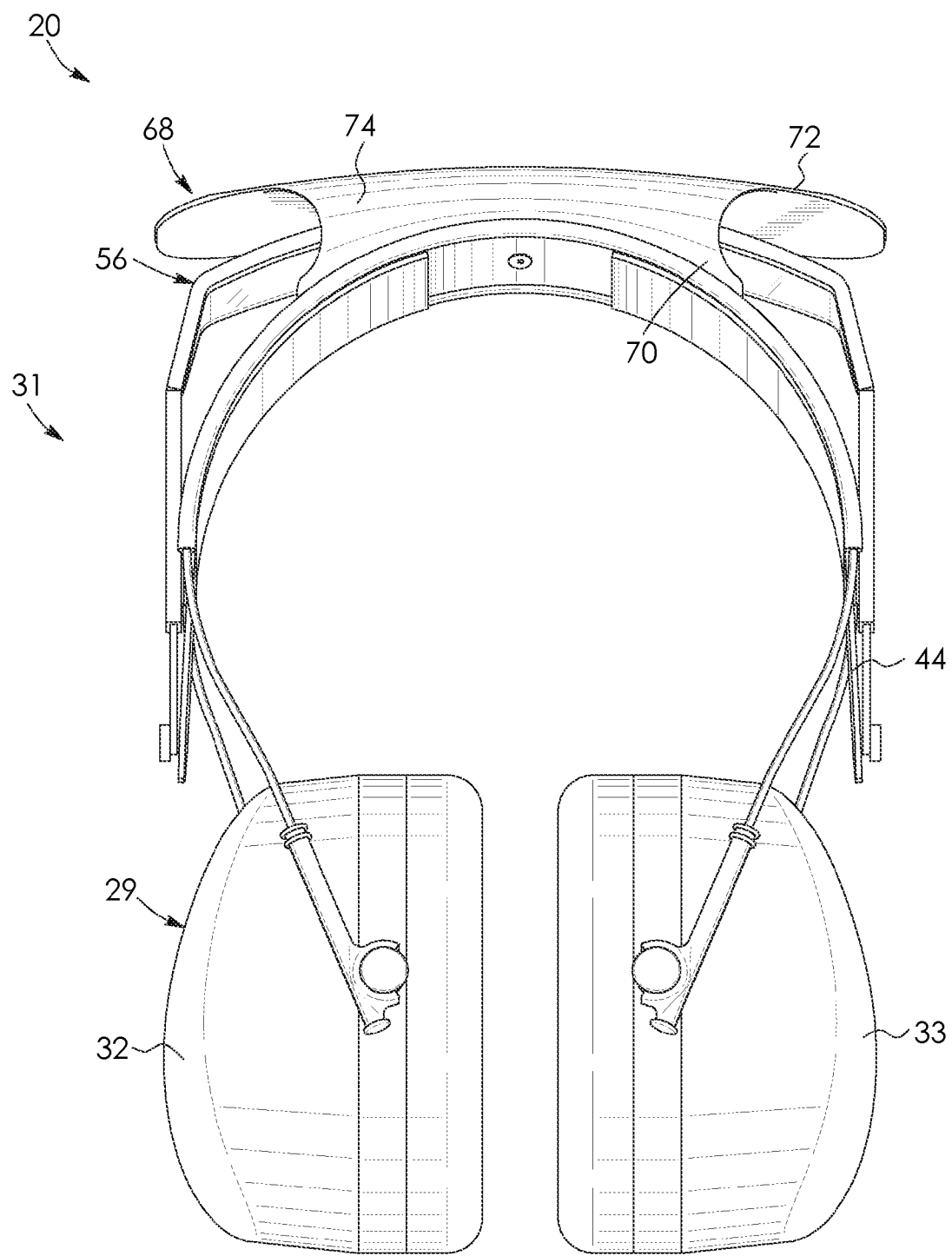
FIG. 5 is a rear elevation view of the assembly shown in FIG. 1.

Referring to the drawings and first to FIG. 1, there is shown an ear-engaging and eye-covering head assembly 20. The assembly has a top 22, a bottom 24 opposite the top, and a pair of spaced-apart sides 26 and 28 extending between the top and the bottom. The assembly 20 also includes a front 30 as best seen in FIG. 3 and a rear 31 opposite the front, as best seen in FIG. 5. Referring to FIG. 1, the front and rear of the assembly extend from top 22 of the assembly to bottom 24 of the assembly.

Figure 4:
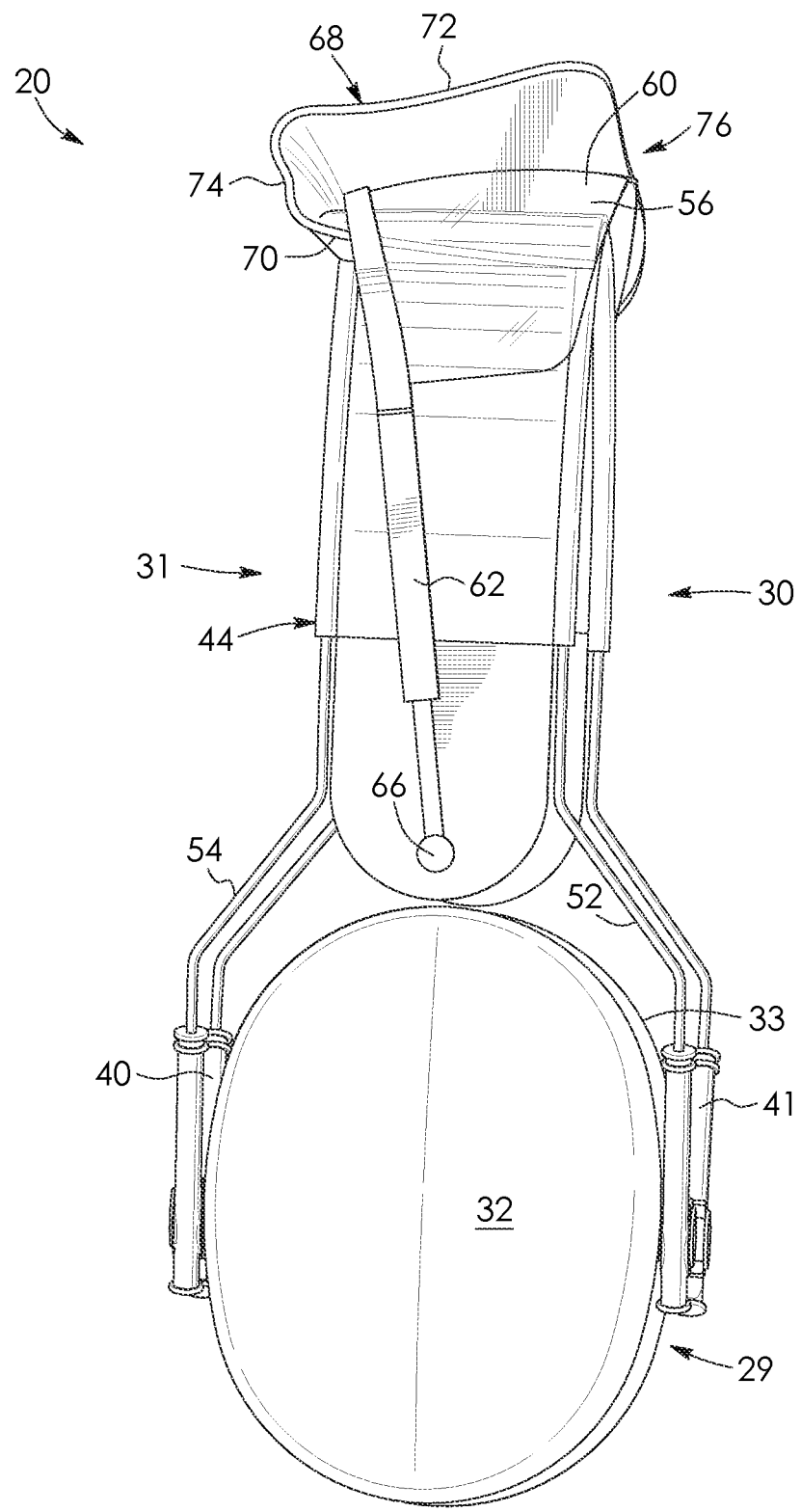
FIG. 4 is a left side elevation view of the assembly shown in FIG. 1.

The assembly 20 includes a pair of ear-engaging members, in this example a pair of ear protectors 29. The ear protectors include earmuffs 32 and 33 for protecting a wearer's ears. Each earmuff is substantially the same in parts and functions and therefore only earmuff 33 will be described in detail. As seen in FIG. 3, earmuff 33 has a top 34 facing top 22 of the assembly 20. Each earmuff has a pair of spaced-apart inner sides and outer sides aligning with the respective sides of the assembly. This is shown by inner side 35 and outer side 36 of earmuff 33, with outer side 36 aligning with side 28 of the assembly 20. As seen in FIG. 1, each earmuff 33 comprises a soft cushion 37 in this example at its inner side. The soft cushion is configured to abut and extend around the wearer's ear. Each earmuff has a centrally-disposed recessed portion 38 in this example within which the wearer's ear may be positioned. Cushion 37 extends around the recessed portion. Each earmuff 33 includes a rigid, dome-like shell 39 in this example at its outer side 36. The shell extends around the cushion. Each earmuff 33 has a pair of spaced-apart tubes 40 and 41 as seen in FIGS. 3 and 4. As seen in FIG. 3, the tubes are positioned between sides 35 and 36 of the earmuffs so as to align with the front 30 and the rear 31 of the assembly 20. The tubes 40 and 41 pivotally connect to the shell 39, as seen by pivot 42 for tube 41 in FIG. 1.

The ear protectors 29 include an arcuate member, in this example a u-shaped, resilient headband 44 operatively connecting the earmuffs 32 and 33 together. The headband is shaped to extend over the top of a wearer's head, such as top 45 of head 47 of wearer 49 shown in FIG. 10. The headband has a pair of spaced-apart ends 46 and 48 positioned adjacent to earmuffs 32 and 33, respectively, as seen in FIG. 1. The headband 44 has a curved top 50 in this example positioned adjacent to top 22 of the assembly. Top 50 is spaced-apart from the ends 46 and 48 of the headband. The headband 44 is configured to rest upon a user's head, with top 50 abutting the top of the user's head. Ends 46 and 48 are configured to abut the sides of the user's head and align adjacent to the user's ears. The headband 44 and earmuffs 32 and 33 as described thus far, with theirs parts and functionings, may be conventional and well known to those skilled in the art.

Referring back to FIG. 1, the assembly 20 includes an adjustment mechanism, in this example two pairs of stiff, arcuate-shaped elongate members, in this example wires that connect headband 44 with earmuffs 32 and 33 and allow the positioning of the earmuffs relative to the headband to be adjusted. This is shown by wires 52 and 54 for earmuff 33 in FIG. 1. The wires are arcuate-shaped and integral with the headband in this example. The respective wires are configured to fit within and slidably engage with respective ones of the tubes 40 and 41 of the earmuffs 32 and 33 to adjust the positioning of the earmuffs.

As seen in FIG. 1, the assembly 20 has an eye-covering member, in this example an eye protector 56 for protecting the user's eyes. The eye protector is operatively connected to and is pivotable relative to the headband 44. The eye protector 56 includes a glasses-type frame 58 upon which is connected an eye covering which is at least partially transparent, in this example plastic lenses 60. The frame has a pair of elongate sides 62 and 64 configured to extend along the sides of the user's head. Distal ends of the sides of the frame 58 pivotally connect to ends 46 and 48 of the headband 44 via pivot points, as shown by pivot 66 for end 67 of side 62 of the frame and end 46 of the headband. The ends of the sides of the frames are positioned between wires 52 and 54 in this example.

Figure 2:
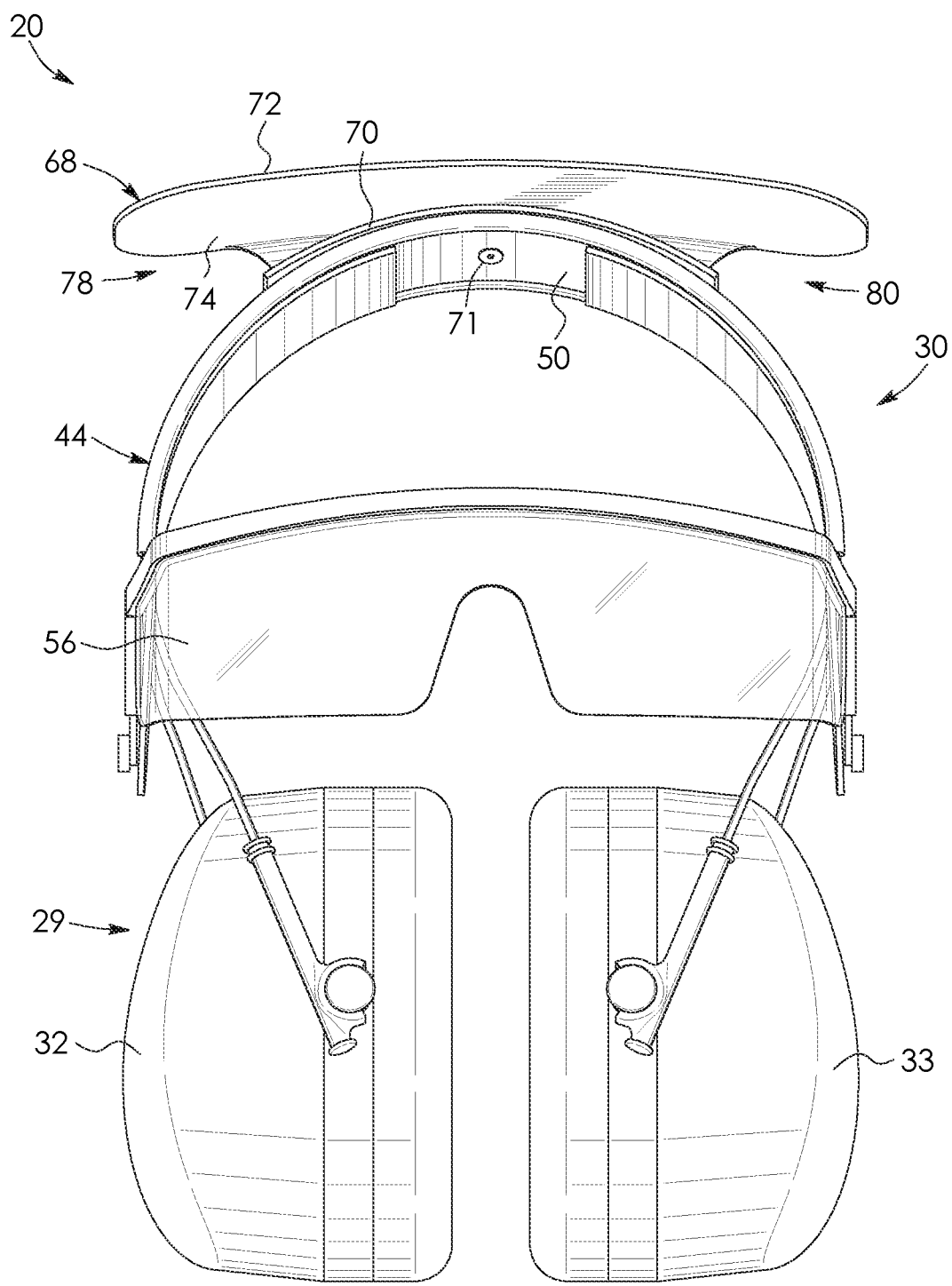
FIG. 2 is a front elevation view of the assembly shown in FIG. 1.

The assembly 20 includes a protective cover 68 connecting to the top 50 of the headband 44 in this example. The ear protectors 29 and protective cover 68 align. The ear protectors 29, protective cover 68 and headband 44 are in the same plane, which is vertically oriented in FIG. 1 and which extends through the ear protectors, protective cover and headband. The protective cover is made of a rigid material in this example, though this is not strictly required. The protective cover 68 is configured to receive, store and protect the eye protector 56. The protective cover is channel-shaped in this example, as shown in FIG. 4. As best seen in FIG. 2, the protective cover 68 has a bottom wall 70 in this example and a top wall 72 spaced-apart from the bottom wall. Each of the walls is arcuate in this example. As seen in FIG. 1, wall 72 has a left side end 77 and a right side end 79 between which the wall extends. The walls 70 and 72 are positioned and spaced-apart for receiving eye protector 56 therebetween when the eye protector is raised, as seen in FIG. 3. Wall 70 has a curvature equal to that of the top of the headband in this example. Also, wall 70 and top 50 of headband 44 have curvatures greater than that of wall 72 in this example.

Referring to FIG. 3, wall 72 has a length L configured to be equal to or longer than the distance between sides 62 and 64 of frame 58 in this example. Bottom wall 70 is connected to top 50 of headband 44 by a connector, in this example by way of a rivet 71. The protective cover 68 has a curved closed rear or back end 74, as best seen in FIGS. 1 and 5, that is generally u-shaped and which connects walls 70 and 72 together. The protective cover has a front opening or open end 76 as seen in FIG. 4 that is spaced-apart from the back end and through which the eye protector 56 passes when raised. As seen in FIG. 4, wall 72 in this example extends at an obtuse angle outwards from back end 74 of the protector towards open end 76. As seen in FIG. 4, the protective cover 68 is angled upwards relative to the bottom wall 70 such that open end 76 of the protective cover is larger than back end 74. Referring to FIGS. 1 and 2, protective cover 68 also has a pair of spaced-apart, side openings 78 and 80 in this example. The side openings of the protective cover 68 extend between walls 70 and 72, with ends 77 and 79 of the wall 72 thus being spaced-apart from and above the pivots 66, thereby at least partially exposing the sides 62 of the eye protector 56 as seen in FIG. 1.

In operation and referring to FIG. 2, the eye protector 56 has a first or lowered position in which the eye protector is angularly spaced-apart from and relative to the headband 44, in this example by 90 degrees. In this position, the eye protector and earmuffs 32 and 33 are configured to align with, engage with and protect the user's eyes and ears. The eye protector 56 is pivotable to a second or raised position, seen in FIGS. 3 to 5, in which the eye protector 56 is disposed within protective cover 68. In this position, as seen in FIG. 3, frame 58 of the eye protector may abut back end 74 of the protective cover. Also in this position, walls 70 and 72 are configured to extend over and protect lenses 60 as seen in FIG. 4. Side openings 78 and 80 of cover 68 align with and receive sides 62 and 64 of frame 58. Thus assembly 20 as herein described enables eye protector 56 to be pivoted upwardly and out of the way when the assembly is not in use. The eye protector 56, including its sides 62 and 64, align with and, in this example, are in parallel with the headband 44, when the eye protector is in the second position. The ear protectors 29, headband 44, eye protector 56 and the protective cover 68 align when the eye protector is in the second position.

When force is directed on eye protector 56 so positioned within cover 68, the exterior, peripheral portions of the cover 68 may withstand and absorb such impact. The eye protector with its cover 68 as herein described may thus inhibit the eye protector from being damaged, scratched and misplaced when the assembly is not in use.

In one embodiment, the protective cover 68 and the headband 44 are integral and in the form of a one-piece moulded unit. In this embodiment, wall 70 of protective cover 68 is not strictly required, as curved top 50 of headband 44 may perform the function of and serve as wall 70.

Figure 6:
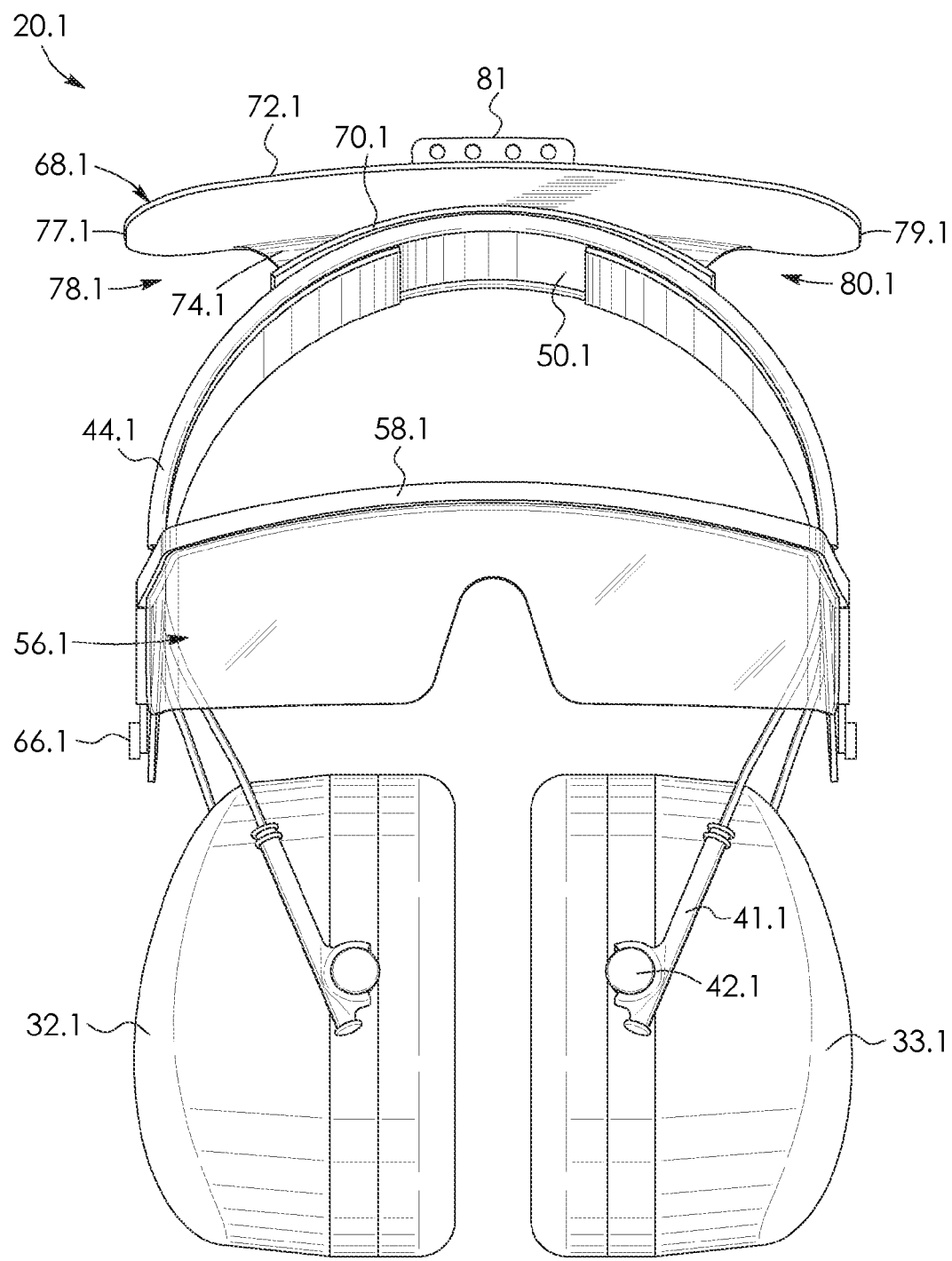
FIG. 6 is a front elevation view of an ear-engaging and eye-covering head assembly according to a second aspect, the assembly including a protective cover, an eye protector shown in a lowered, first position and a light apparatus connected to the protective cover.

FIG. 6 shows an ear and eye protector head assembly 20.1 according to a second aspect. Like parts have like numbers and functions as the assembly shown in FIGS. 1 to 5 with the addition of "0.1". Assembly 20.1 is substantially the same as assembly 20 shown in FIGS. 1 to 5 with the following exceptions. The assembly includes a light apparatus, in this example a plurality of lights, in this example light-emitting diode (LED) lights 81 disposed on the top 72.1 of the protective cover 68.1 in this example. There may be a battery pack mounted in or on assembly 20 for the lights. Portable LED lights per se, including their parts and functionings, are well known to those skilled in the art and therefore will not be described in further detail.

Figure 7:
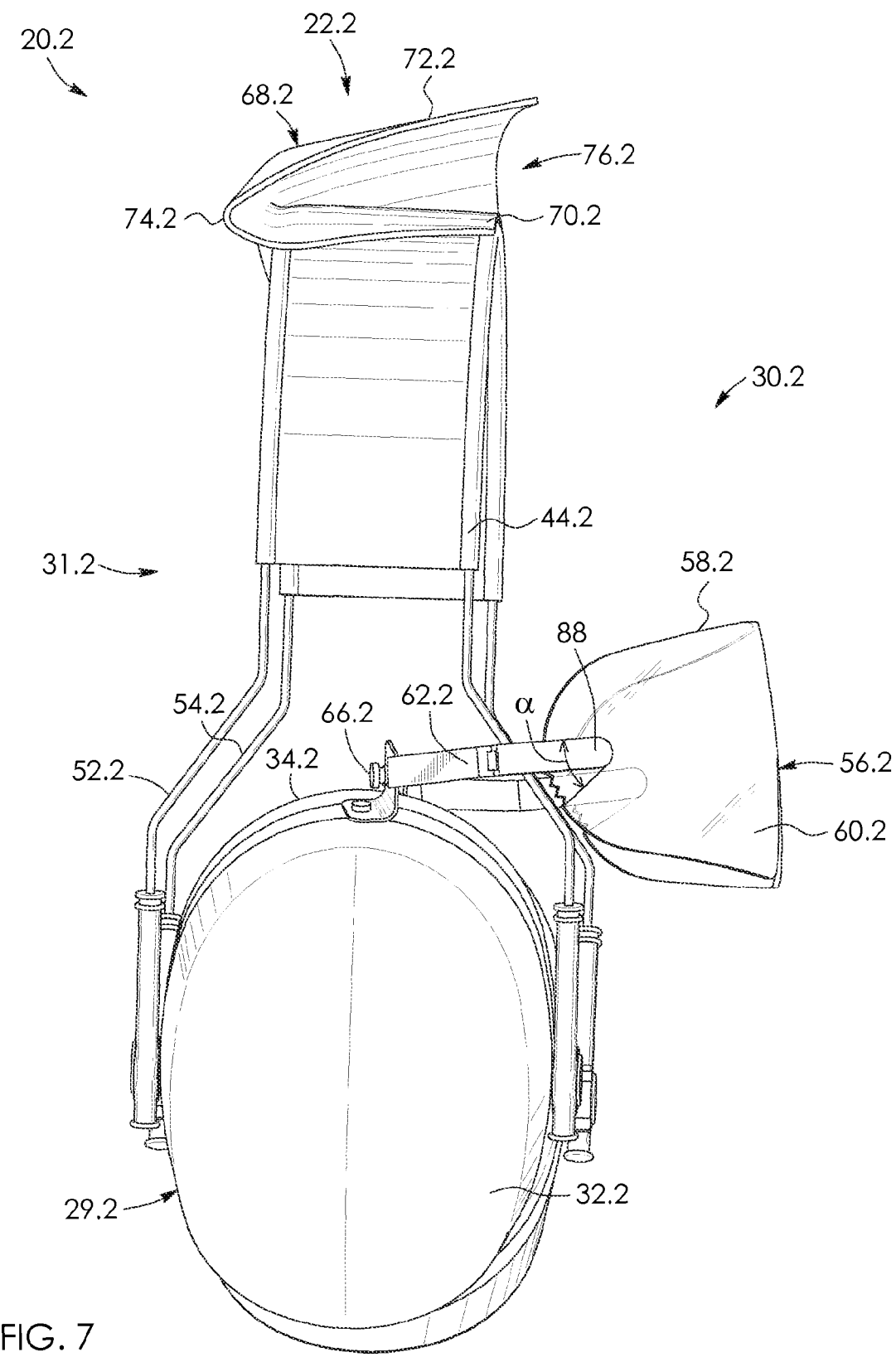
FIG. 7 is a left side elevation view of an ear-engaging and eye-covering head assembly according to a third aspect, the assembly including a protective cover and including an eye protector shown in a lowered, first position.
Figure 8:
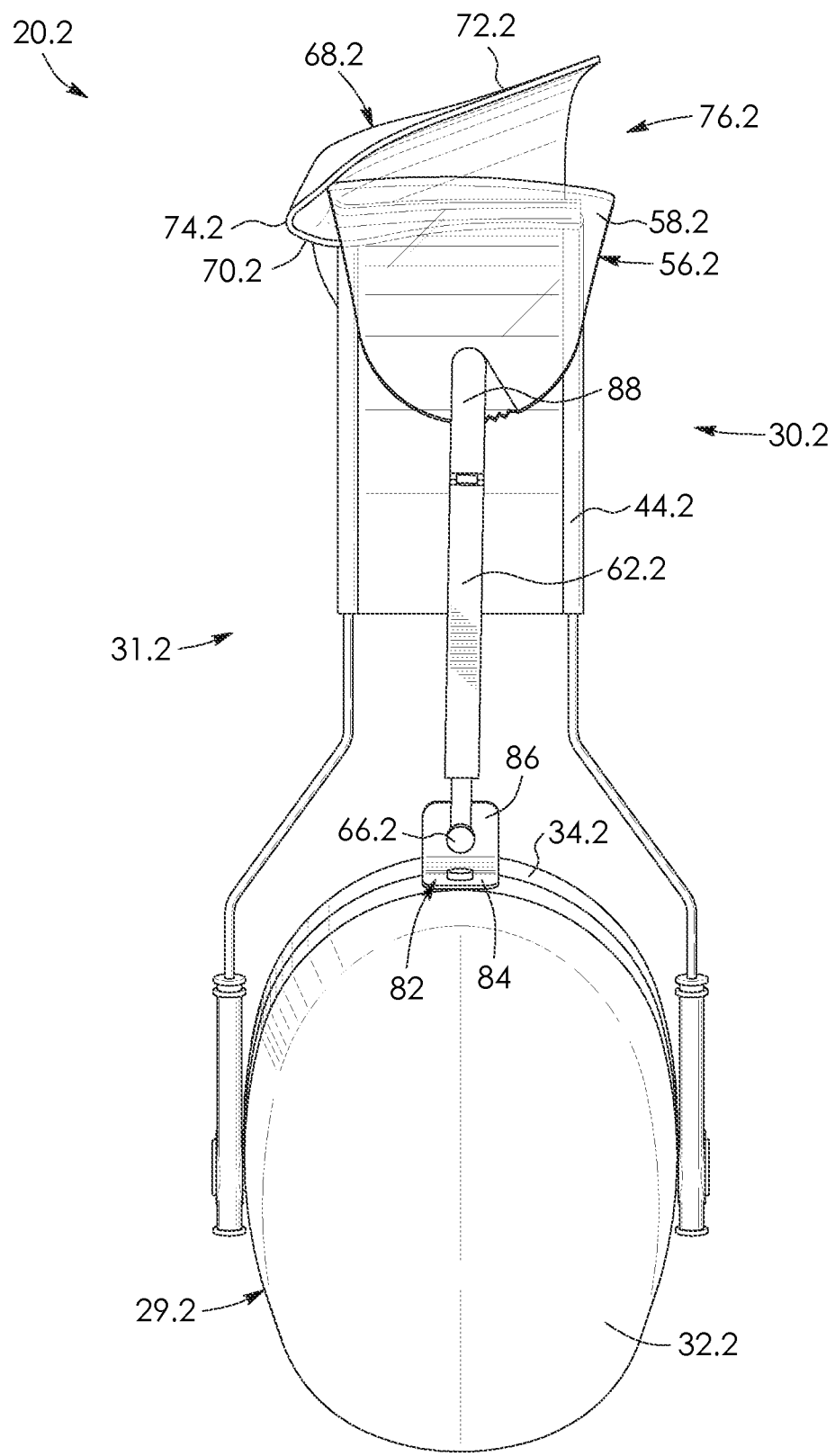
FIG. 8 is a left side elevation view of the assembly shown in FIG. 7, with the eye protector being positioned within the protective cover in a raised, second position.
Figure 9:
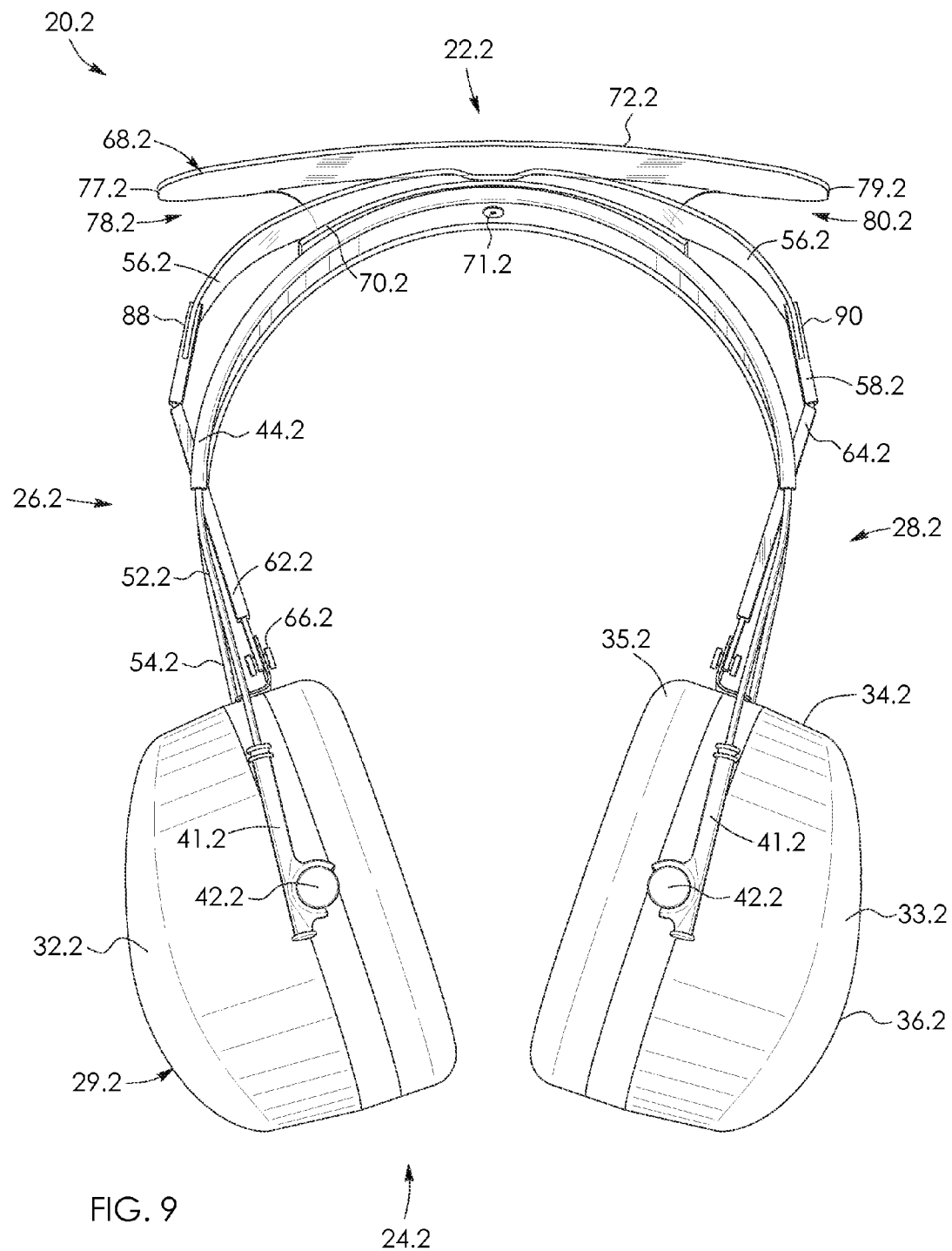
FIG. 9 is a front elevation view of the assembly shown in FIG. 8.

FIGS. 7 to 9 show an ear and eye protector head assembly 20.2 according to a third aspect. Like parts have like numbers and functions as the assembly shown in FIGS. 1 to 5 with the addition of "0.2". Assembly 20.2 is substantially the same as assembly 20 shown in FIGS. 1 to 5 with the following exceptions. The assembly includes a pair of connectors, in this example L-shaped brackets connected to the tops 34.2 of the earmuffs 32.2 and 33.2, as shown by bracket 82 for earmuff 32.2. Referring to FIG. 8, each of the brackets has a first portion that connects to its respective earmuff and a second portion angled at 90 degrees relative to the first portion in this example, as shown by first portion 84 and second portion 86 for bracket 82. The second portions 86 of the brackets 82 pivotally connect to the sides 62.2 and 64.2 of the eye protector 56.2, respectively.

As seen in FIG. 7, protective cover 68.2 is v-shaped in cross-section in this example.

As seen in FIGS. 7 and 9, eye protector 56.2 has a pair of adjustment mechanisms, in this example pivots 88 and 90 that pivotally connect plastic lenses 60.2 to sides 62.2 and 64.2. The pivots allow the plastic lenses to be selectively angularly adjusted within an angular span a relative to frame 58.2, as best seen in FIG. 7, with different locking configurations that operate through friction in their pivot 88 and 90 in this example. Eye protectors having such an adjustment mechanism per se, including their parts and functionings, are well known to those skilled in the art and therefore will be described in further detail.

Figure 10:
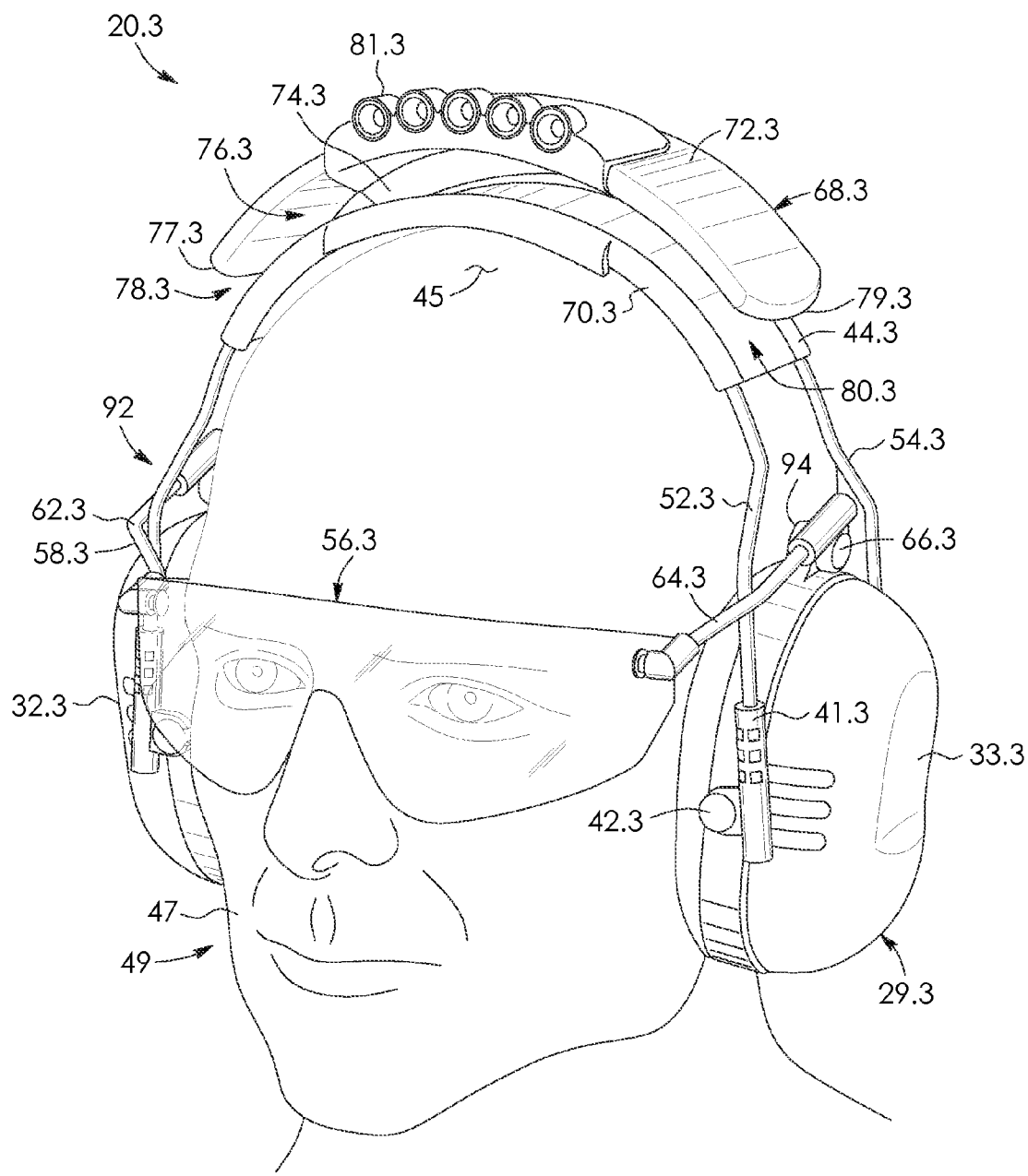
FIG. 10 is a front perspective view of an ear-engaging and eye-covering head assembly according to a fourth aspect, the assembly including a protective cover and including an eye protector shown in a lowered, first position.

FIG. 10 shows an ear and eye protector head assembly 20.3 according to a fourth aspect. Like parts have like numbers and functions as the assembly shown in FIGS. 1 to 5 with the addition of decimal extension "0.3". Assembly 20.3 is substantially the same as assembly 20 shown in FIGS. 1 to 5 with some exceptions. Also, lights 81.3 are similar to lights 81 shown in FIG. 6. The lights 81.3 together with the protective cover 68.3 and headband 44.3 are integrally formed as a single part in this example. The curvatures of walls 70.3 and 72.3 of protective cover 68.3 are substantially equal to each other in this example.

Assembly 20.3 includes a further pair of adjustment mechanisms, in this example pivoting tubes 92 and 94 that connect to and extend from respective pivots 66.3. Sides 62.3 and 64.3 of frame 58.3 of the eye protector 56.3 are in the form of wires partially disposed within the tubes 92 and 94. The tubes allow the eye protector to selectively retract inwards or extend outwards relative to headband 44.3. Positioning of the eye protector relative to the wearer's face thereby may be selectively adjusted.

Alternatively, the sides of the frames of the eye protector may be in tube form and slidably engage with elongate members, such as wires, that pivotally connect to and extend from respective ends of the earmuffs and/or headband. In the example shown in FIG. 10, sides 62.3 and 64.3 pivotally connect to earmuffs 32.3 and 33.3.

In a further alternative, the sides of the frame may pivotally connect to the headband in a manner otherwise substantially similar to that shown for assembly 20 in FIGS. 1 to 5.

The assembly as herein described may be useful for protecting a user's eyes and ears in a wide variety of applications. For example, the assembly may be useful for homeowners when mowing the lawn, string trimming weeds, leaf blowing, power washing, splitting wood, chainsawing and landscaping. The assembly may also be useful in the construction industry, for carpentry work with power tools, finishing carpenters, cabinet makers, framers, brush trimming, cutting and setting tiles, stone masons, brick layers, and wood floor installers, for example. The assembly may further be useful in the automotive and aviation industries, for military applications, for fire and police departments, for heavy equipment operators and when using loud machines generally. It may be yet further useful for protecting a user's eyes and ears during recreational and sports activities, such as gaming, car racing, hunting, and shooting, including for shooting ranges. The eye protector may be in the form of sunglasses or prescription eyeglasses.

Figure 11:
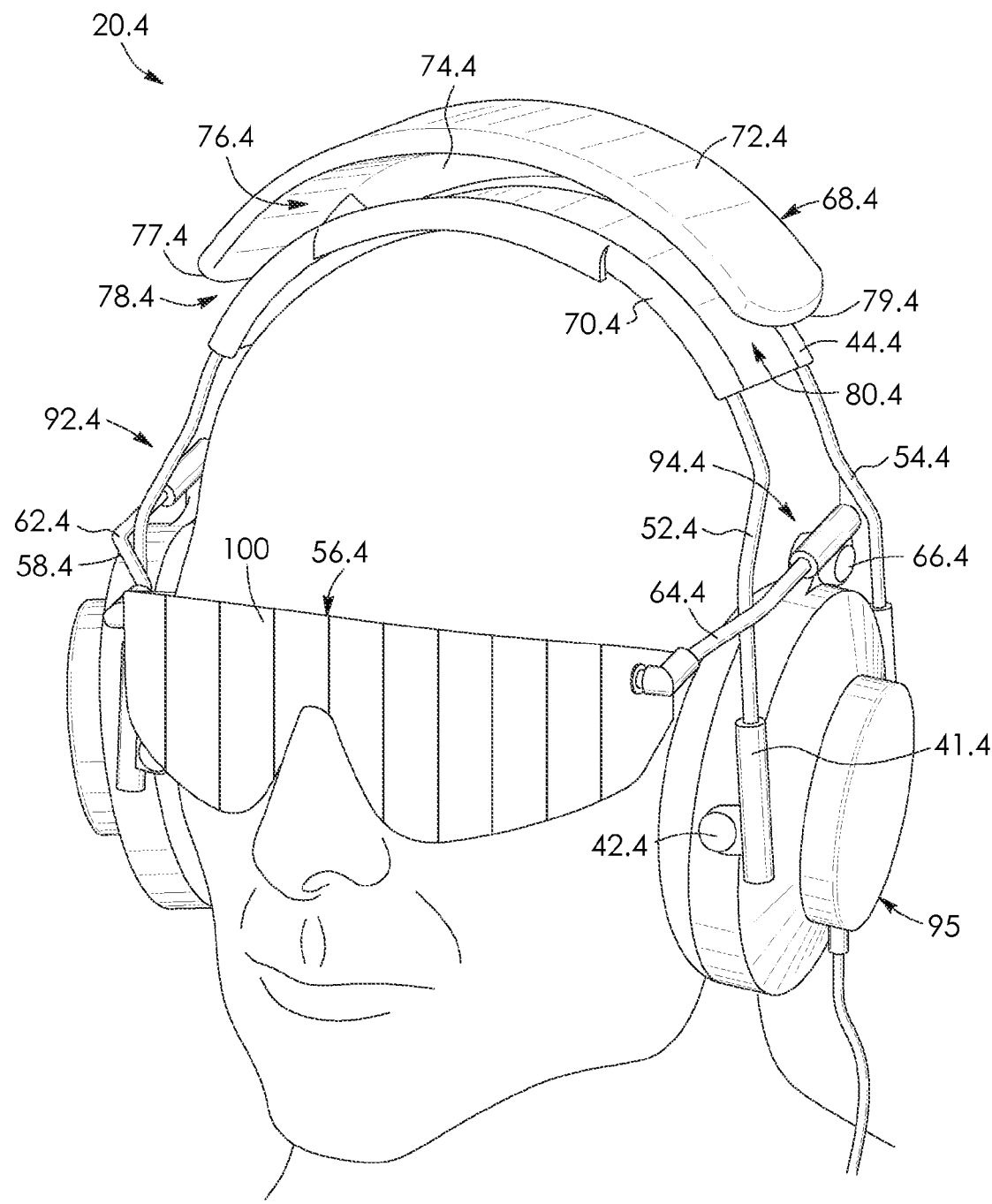
FIG. 11 a front perspective view of an ear-engaging and eye-covering head assembly according to a fifth aspect.

FIG. 11 shows an ear and eye covering head assembly 20.4 according to a fifth aspect. Like parts have like numbers and functions as the assembly shown in FIG. 10 with decimal extension "0.4" replacing "0.3" and decimal extensions "0.4" being added to numerals not previously having decimal extensions. Assembly 20.4 is substantially the same as assembly 20.3 shown in FIG. 10 with the following exceptions. Instead of ear muffs 32.4 and 33.4, the ear-engaging members are headphones 95. Also, the assembly's eye-covering member 56.4 includes a video display assembly 100. The video display assembly may be for use as a virtual reality visor or a display unit, for example. The assembly 100 may be used in the form of a portable movie player, a gaming system and/or portable home stereo system. Earphones and video display assemblies per se are well known to those skilled in the art and therefore will not be described in further detail.

Figure 14:
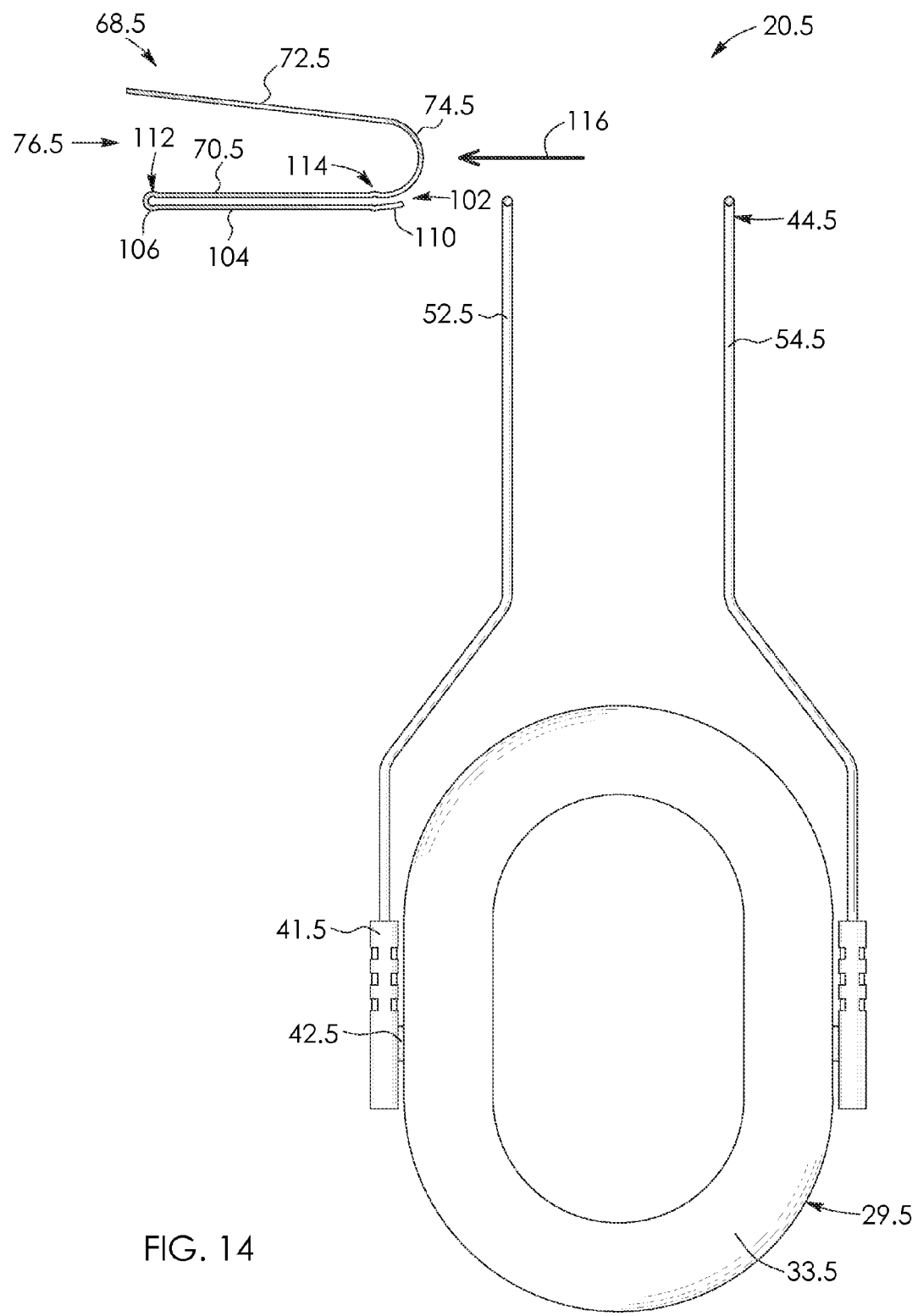
FIG. 14 is a side elevation view of the ear-engaging and eye-covering assembly according to the sixth aspect, the protective cover being shown in section and in the process of connecting to the rest of the assembly.
Figure 15:
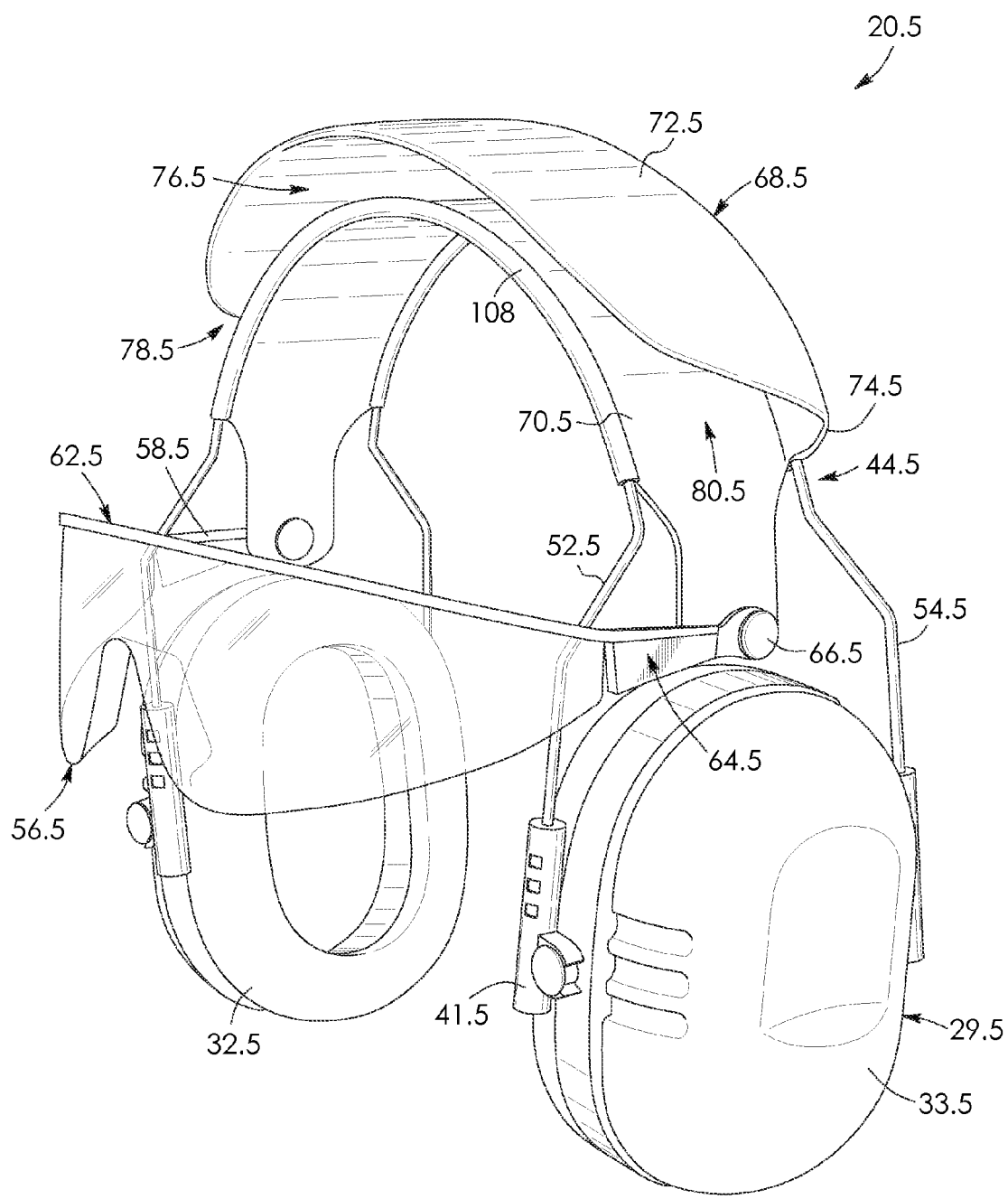
FIG. 15 is a front perspective view of the ear-engaging and eye-covering head assembly according to the sixth aspect, the protective cover being shown connected to the rest of the assembly.

FIGS. 12 to 15 show an ear and eye covering head assembly 20.5 according to a sixth aspect. Like parts have like numbers and functions as the assembly shown in FIG. 6 with decimal extension "0.5" replacing "0.1" and decimal extensions "0.5" being added to numerals not previously having decimal extensions. Assembly 20.5 is similar to assembly 20.1 shown in FIG. 10 with the following exceptions. The assembly includes a protective cover 68.5 that may selectively slip on to and off of the headband of an existing, off-the-shelf pair of ear-engaging members such as earmuffs 32.5 and 33.5. The headband comprises a pair of wires 52.5 and 54.5 in this example as shown in FIG. 15 that connect the earmuffs together. However, this is not strictly required and the headband may be formed of other materials and comprise other shapes in other embodiments.

Figure 12:
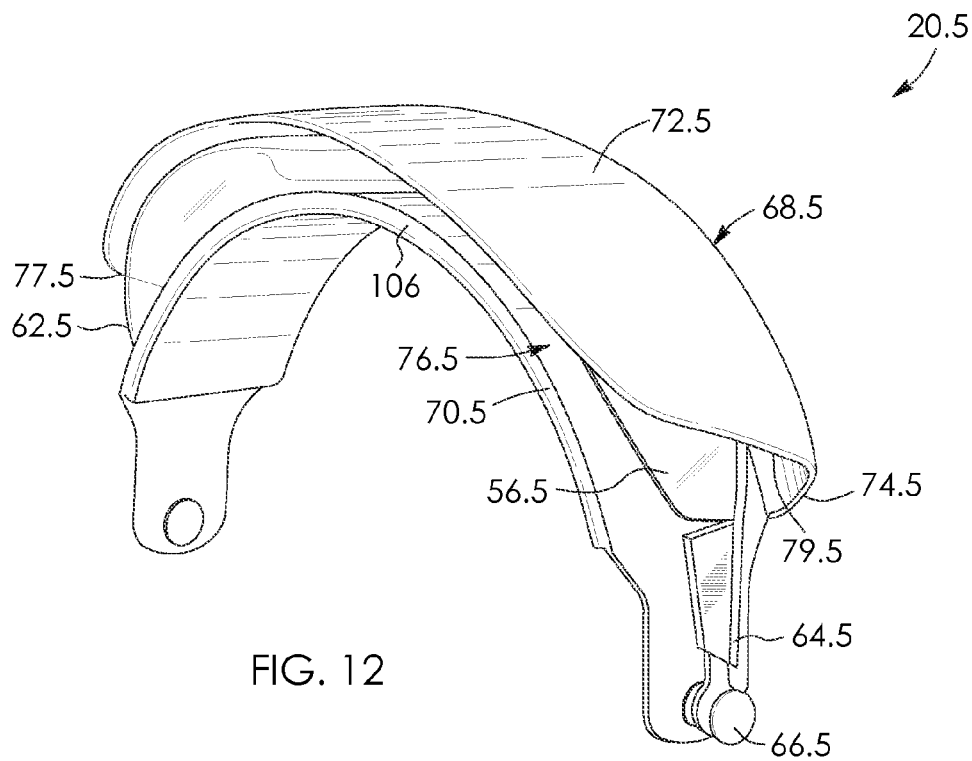
FIG. 12 is a front, side perspective view of a protective cover for an ear-engaging and eye-covering head assembly according to a sixth aspect.
Figure 13:
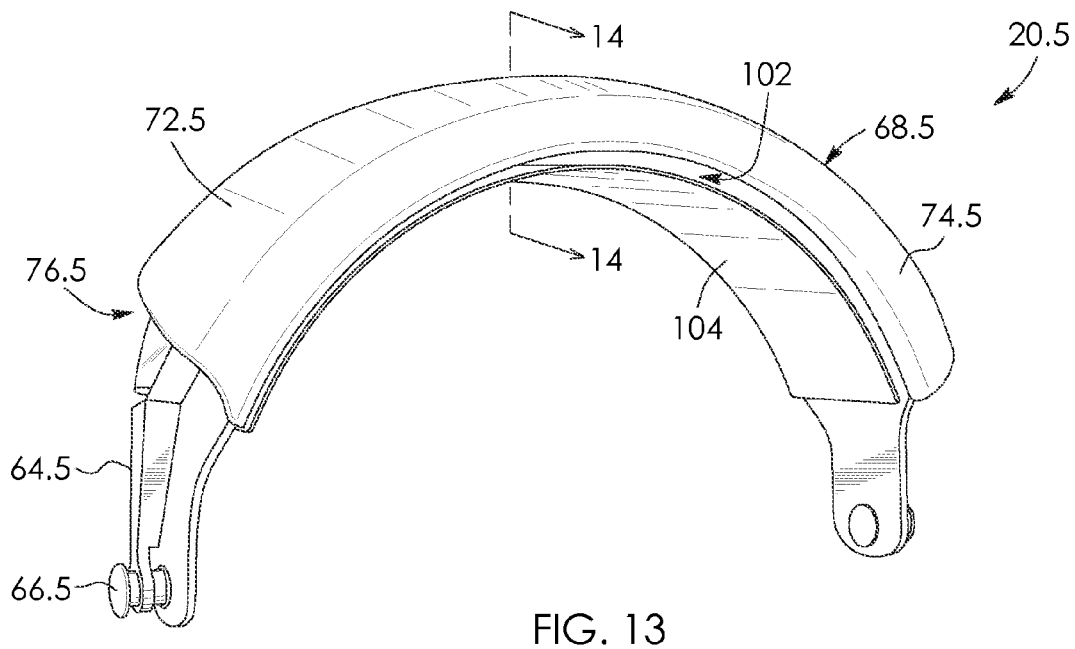
FIG. 13 is a rear perspective view of the protective cover of FIG. 12.

As seen in FIG. 14, eye protector 68.5 is s-shaped in side cross-section and includes an arcuate-shaped slotted portion 102 formed between a pair of spaced-apart arcuate-shaped walls 70.5 and 104 which are connected together at a first, closed end 106. Referring to FIG. 12, end 106 is arcuate-shaped and aligns with open end 76.5 of the eye protector 68.5 in this example. As seen in FIG. 14, wall 104 extends from end 106 to a second end 110 spaced-apart from end 106. End 110 is adjacent to the back end 74.5 of the protector 68.5 in this example.

The eye protector 68.5 has a pair of spaced-apart arcuate-shaped recessed portions 112 and 114 aligned by ends 106 and 110, respectively. Slotted portion 102 is configured to receive headband 44.5, as shown by arrow of numeral 116, with recessed portions 112 and 114 configured to selectively receive wires 52.5 and 54.5, respectively. The eye protector 68.5 may be slid onto the wires of an off-the-shelf headband thereby. Wall 104 may be lowered downwards and spaced-apart from wall 70.5 to selectively from the wires from the eye protector in order to remove the eye protector from the headband.

Figure 16:
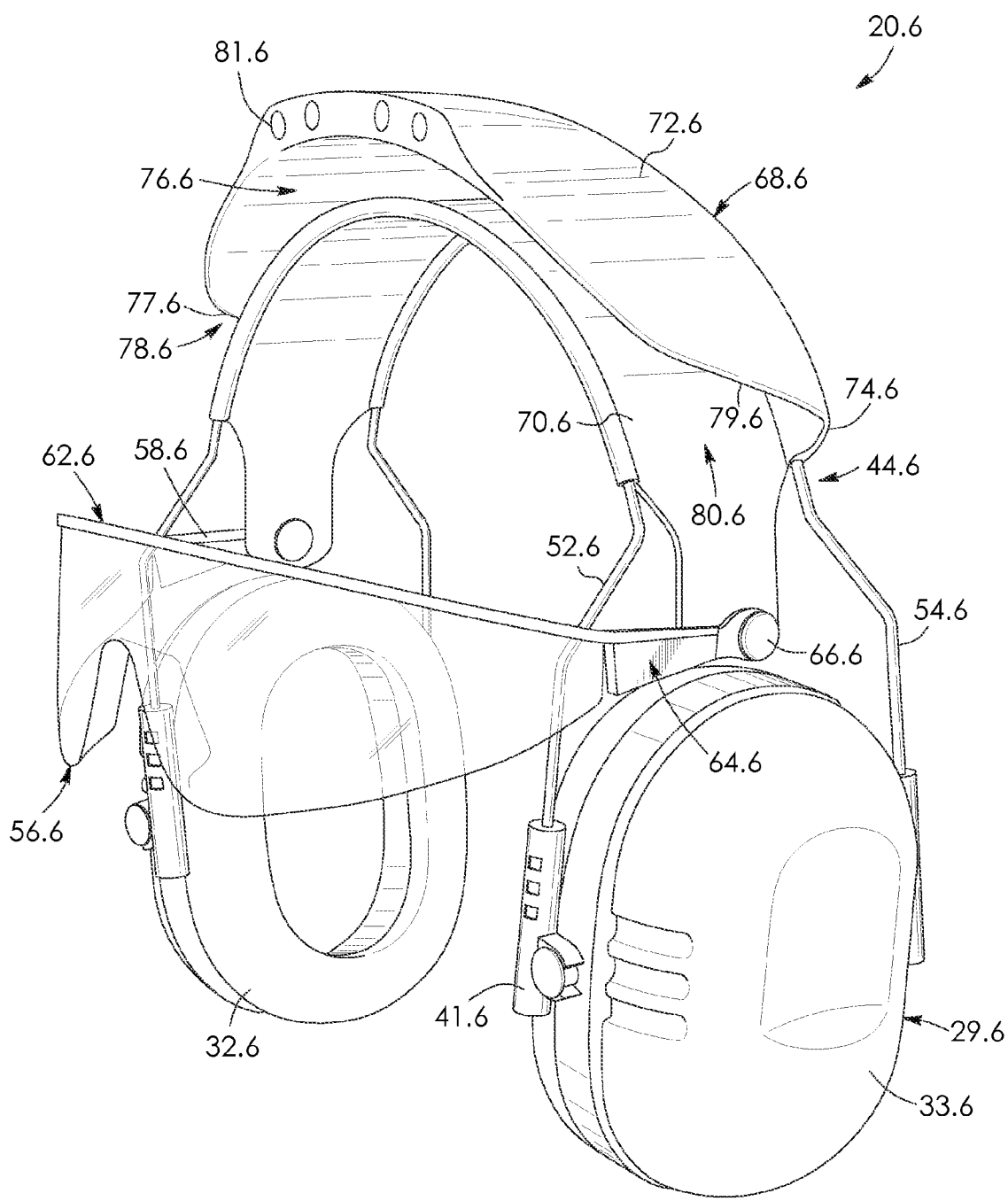
FIG. 16 is a front perspective view of the ear-engaging and eye-covering head assembly according to the seventh aspect.

FIG. 16 shows an ear and eye covering head assembly 20.6 according to a seventh aspect. Like parts have like numbers and functions as the assembly shown in FIGS. 12 to 15 with decimal extension "0.6" replacing "0.5". Assembly 20.6 is similar to assembly 20.5 shown in FIGS. 12 to 15 with the exception that it includes lights 81.6 substantially the same as lights 81 shown in FIG. 6 for assembly 20.1, the lights being integrally formed with the top wall 72.6 of the eye protector 68.6.

Figure 17:
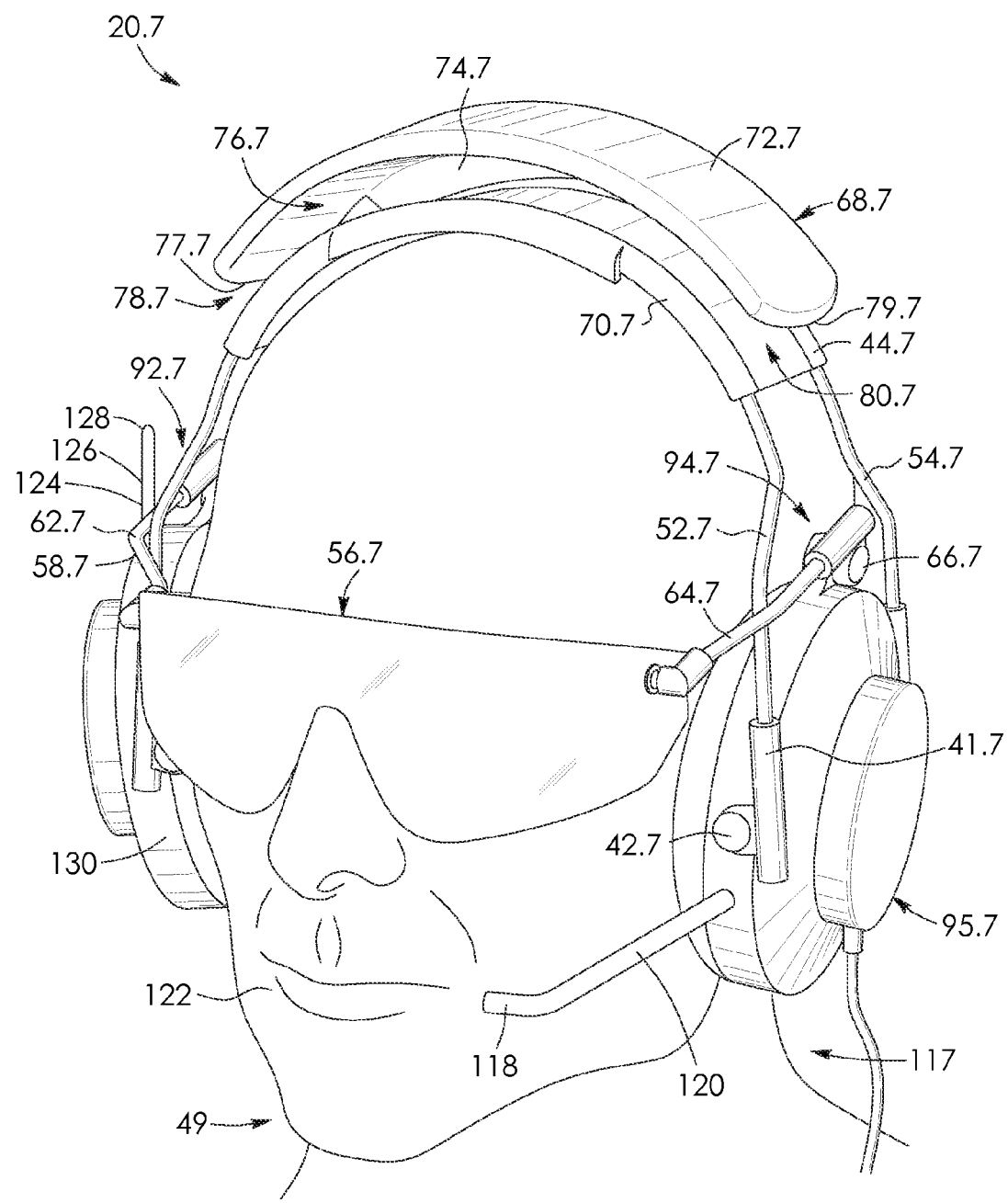
FIG. 17 is a front perspective view of an ear-engaging and eye-covering head assembly according to an eight aspect.

FIG. 17 shows an ear and eye covering head assembly 20.7 according to an eighth aspect. Like parts have like numbers and functions as the assembly shown in FIG. 11 with decimal extension "0.7" replacing "0.4" and decimal extensions "0.7" being added to numerals not previously having decimal extensions. Assembly 20.7 is substantially the same as assembly 20.4 shown in FIG. 11 with the following exceptions. The assembly includes a communication system 117. The communication system has a microphone 118 that connects to and extends from the headphone 95.7 via an elongated rod 120 in this example. The microphone is positioned adjacent to the wearer's mouth 122 and receives voice communications from the wearer 49 of the assembly 20.7. The communication system 117 includes a transmitter 124 for transmitting a signal based on the communications received by the microphone 118. The system includes a receiver 126 for receiving an audio signal transmitted from an external source. Instead of a transmitter and a receiver, a transceiver may be provided. The system 117 includes an antenna 128 connected to and extending outwards from one of the headphones 95.7 in this example. The communication system 117 includes speakers 130 which are a part of the headphones 95.7, respectively. The transmitter 124, receiver 126 and antenna 128 are operatively connected to the microphone 118 and the speakers 130. The communication system in this example is conventional and its parts and functionings will therefore not be described in further detail.

Assembly 20.7 includes headphones 95.7. In the alternative, assembly 20.7 may include ear protectors 29 having earmuffs 32 and 33 such as those shown for assembly 20 in FIGS. 1 to 5.

FIGS. 18 to 23 show an ear and eye covering head assembly 20.8 according to a ninth aspect. Like parts have like numbers and functions as the assembly shown in FIG. 6 with decimal extension "0.8" replacing "0.1" and decimal extensions "0.8" being added to numerals not previously having decimal extensions. Assembly 20.8 is similar to assembly 20.1 shown in FIG. 10 with the following exceptions.

Figure 18:
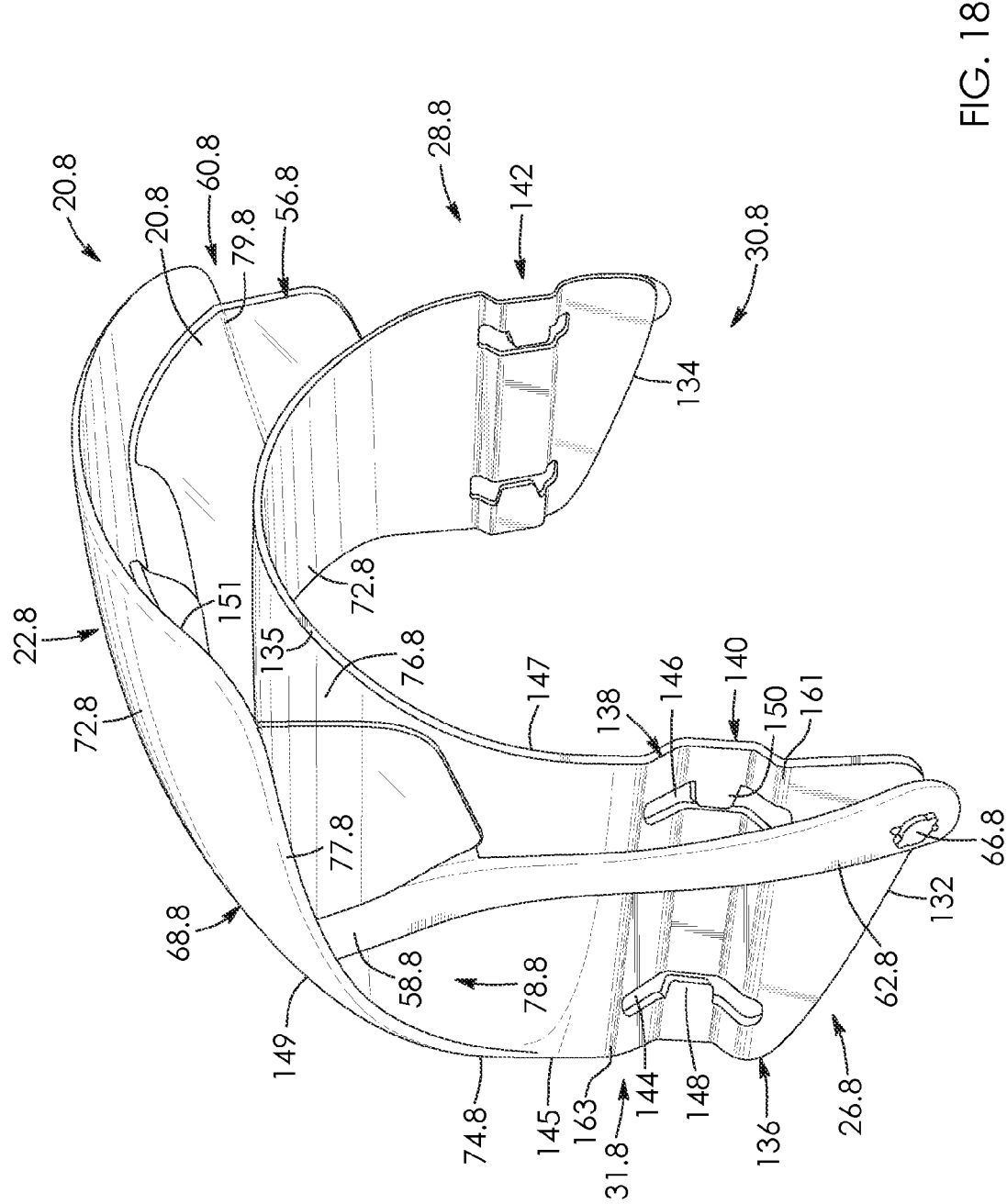
FIG. 18 is a front, side perspective view of a protective cover and eye protector pivotally connected thereto for an ear-engaging and eye-covering head assembly according to a ninth aspect, with the eye protector being shown in a raised, second position.

As seen in FIG. 18, the protective cover 68.8 has lower ends 132 and 134 to which the eye-protector 56.8 pivotally connects. The lower ends may be referred to as the lower ends of bottom wall 70.8 Arcuate-shaped bottom wall 70.8 of the protector cover 68.8 has a curved upper end 135 spaced-apart from and interposed between the lower ends. The bottom wall has a pair of spaced-apart, arcuate-shaped front and rear peripheral portions 145 and 147 extending between ends 132 and 134.

Figure 19:
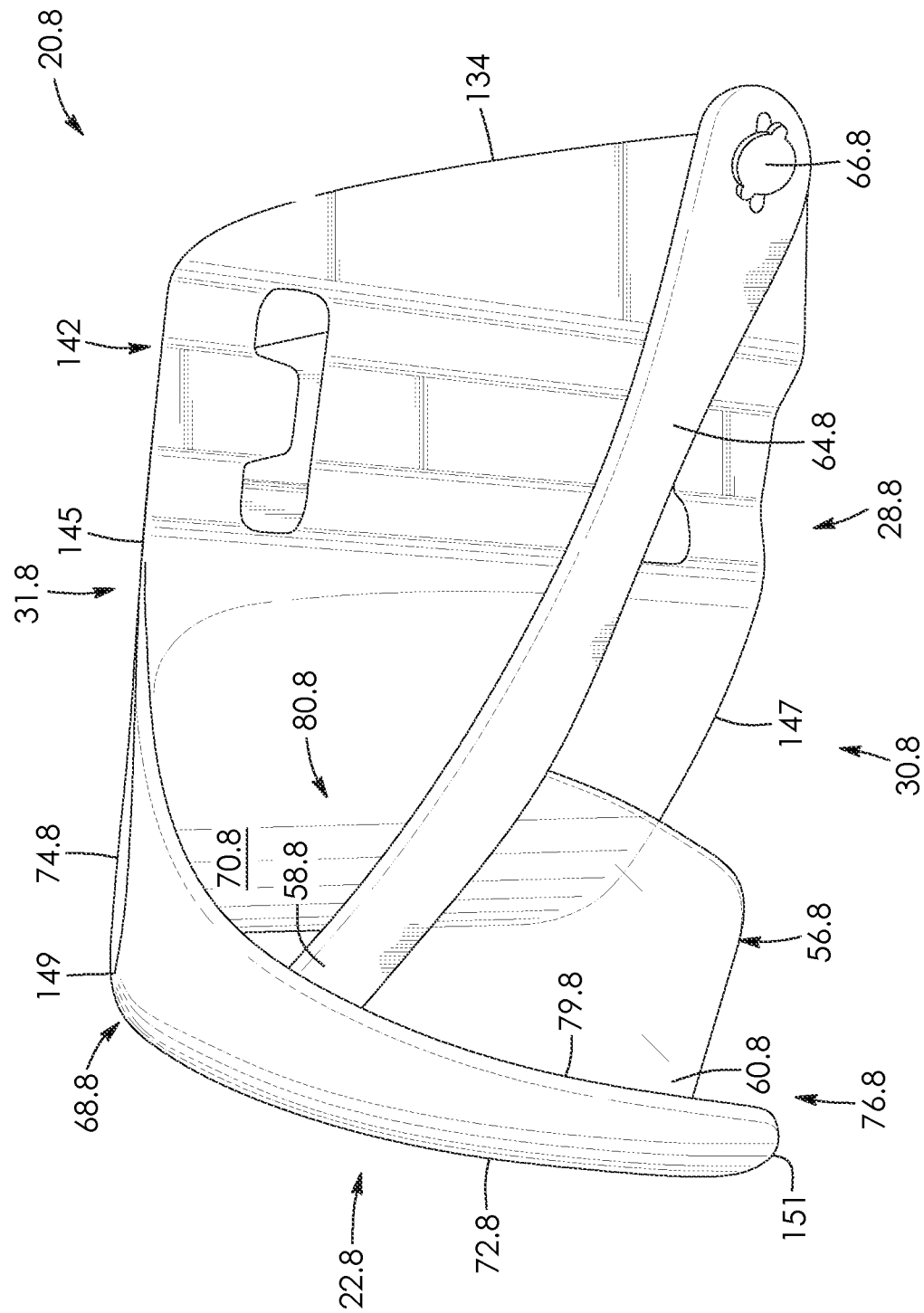
FIG. 19 is a perspective view of the protective cover and eye protector of FIG. 18, with the cover being shown resting on its side and with eye protector enclosed therewithin.

Side ends 77.8 and 79.8 of the top wall 72.8 of the protective cover 68.8 are spaced-apart above the lower ends 132 and 134 of the protective cover. The top wall has a pair of spaced-apart, arcuate-shaped front and rear peripheral portions 149 and 151 extending side ends 77.8 and 79.8. As seen in FIG. 19, the rear peripheral portion 151 of the top wall couples to the rear peripheral portion 145 of the bottom wall 70.8 of the protective cover 68.8. The front peripheral portion 149 of the top wall 72.8 aligns with and is spaced-apart above the front peripheral portion 147 of the bottom wall 70.8. Front opening 76.8 is thus formed thereby for receiving the eye protector 56.8 therethrough.

Figure 21:
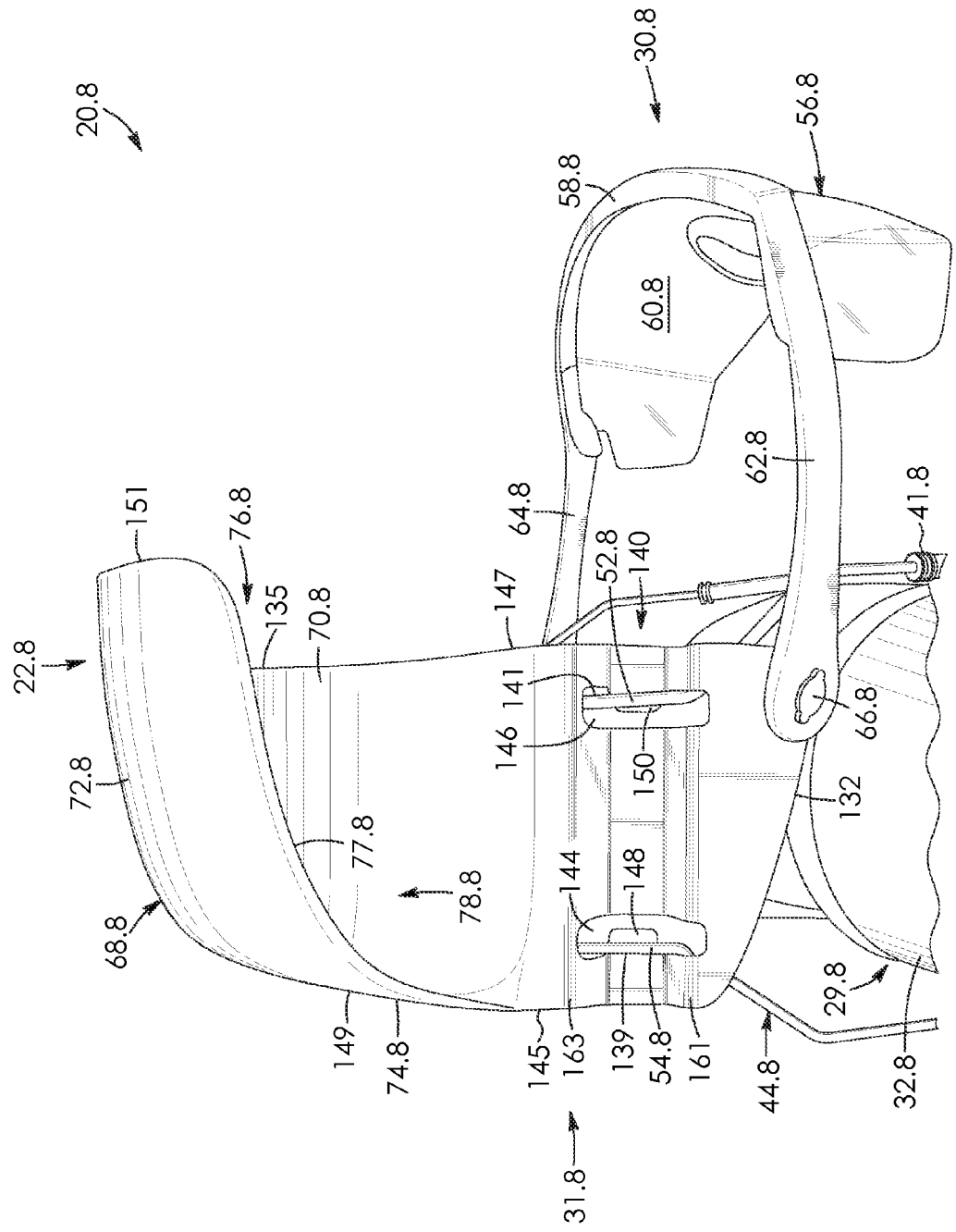
FIG. 21 is a side elevation view of the protective cover and eye protector of FIG. 20, with the ear-engaging and eye-covering head assembly according to the ninth aspect shown in fragment, with the ear protector thereof shown coupled to the protective cover.
Figure 22:
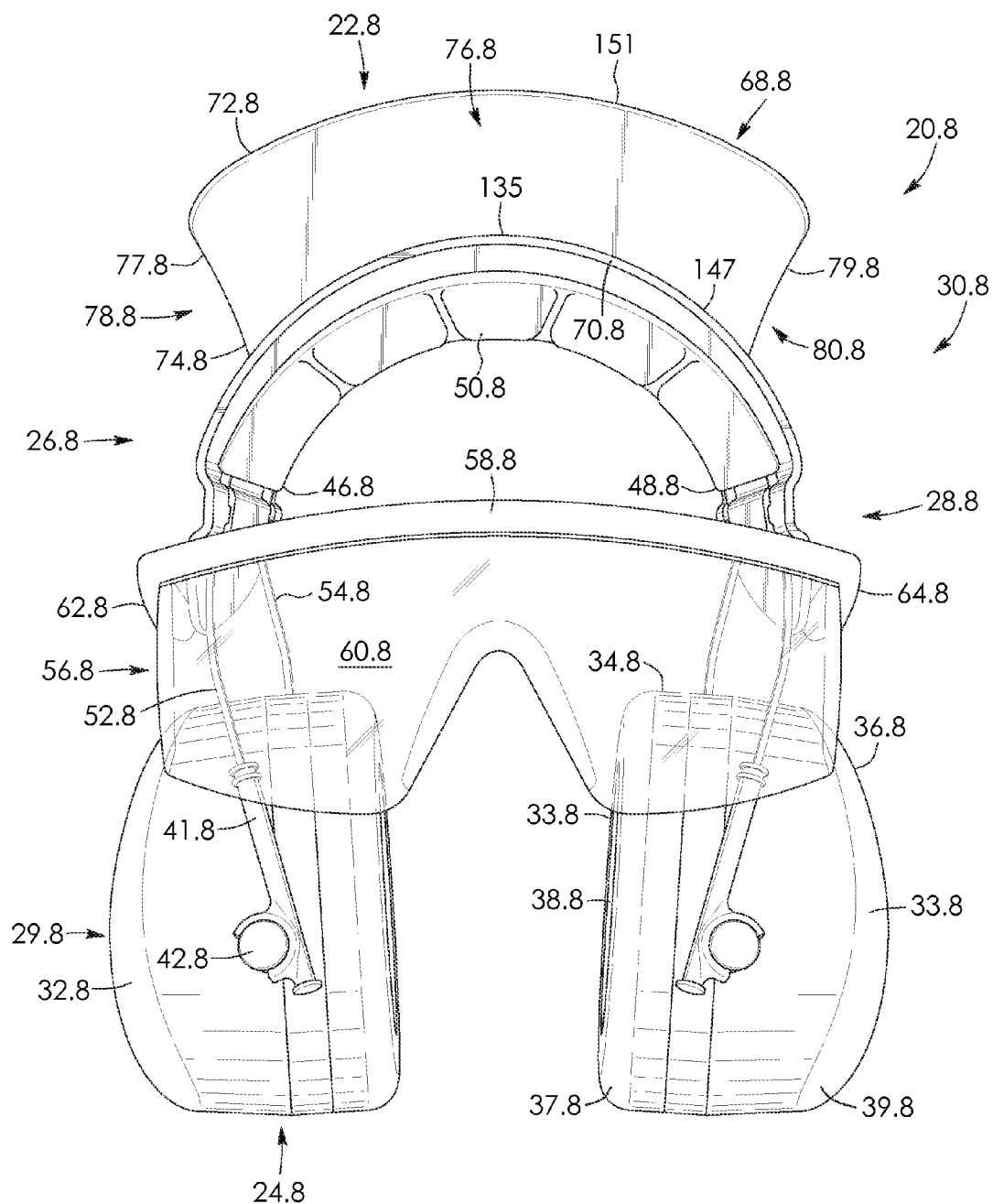
FIG. 22 is a front perspective view of the ear-engaging and eye-covering head assembly of FIG. 21, with the eye protector being shown in the lowered, first position.
Figure 23:
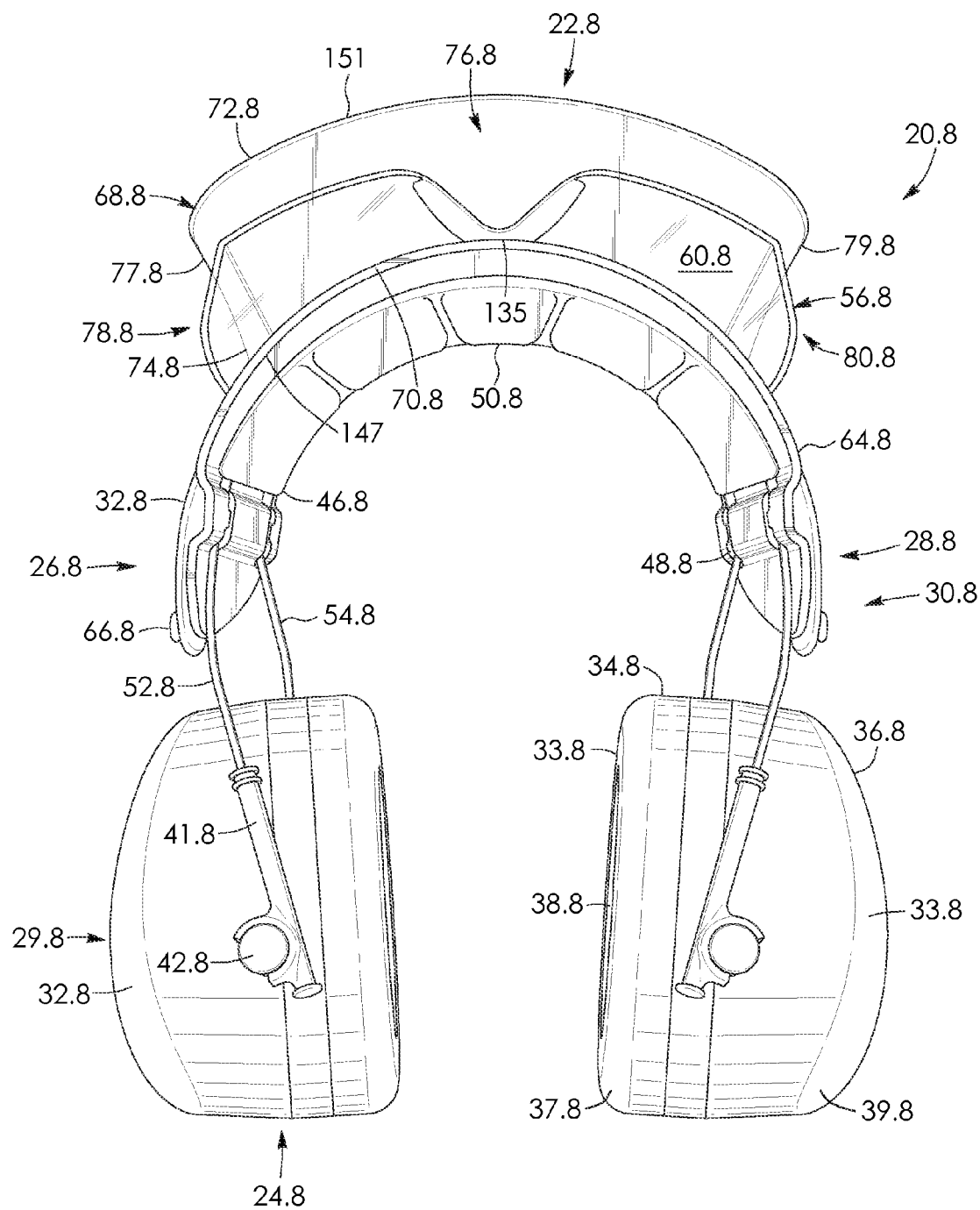
FIG. 23 is a front perspective view of the ear-engaging and eye-covering head assembly of FIG. 22, with the eye protector being shown in the raised, second position.

As seen in FIG. 18, the assembly 20.8 includes a pair of connector mechanisms per end of the eye-protector, as seen by connector mechanisms 136 and 138 for end 132. The connector mechanisms selectively couple the protective cover 68.8 to a hearing protector, in this example ear protectors 29.8, as seen in FIGS. 21 to 23. As seen in FIG. 21, the connector mechanisms 136 and 138 are positioned at the lower ends of the protective cover 68.8 and are shaped to hook around outer portions 139 and 141 of headband 44.8 of the ear protectors 29.8. In this example, the connector mechanisms hook around arcuate-shaped elongate members, in this example wires 52.8 and 54.8 of the headband, though this is not strictly required and the invention may connect to headbands of other forms in other examples.

As seen in FIG. 18, the protective cover 68.8 includes a pair of spaced-apart inwardly-extending protrusions 140 and 142 adjacent to the lower ends 132 and 134 thereof. As seen in FIG. 21, the inwardly-extending protrusions are shaped for selectively coupling headband portions 52.8 and 54.8 of the headband 44.8 of the hearing or ear protectors 29.8. Each of the protrusions is shaped as an outwardly-facing channel.

Figure 20:
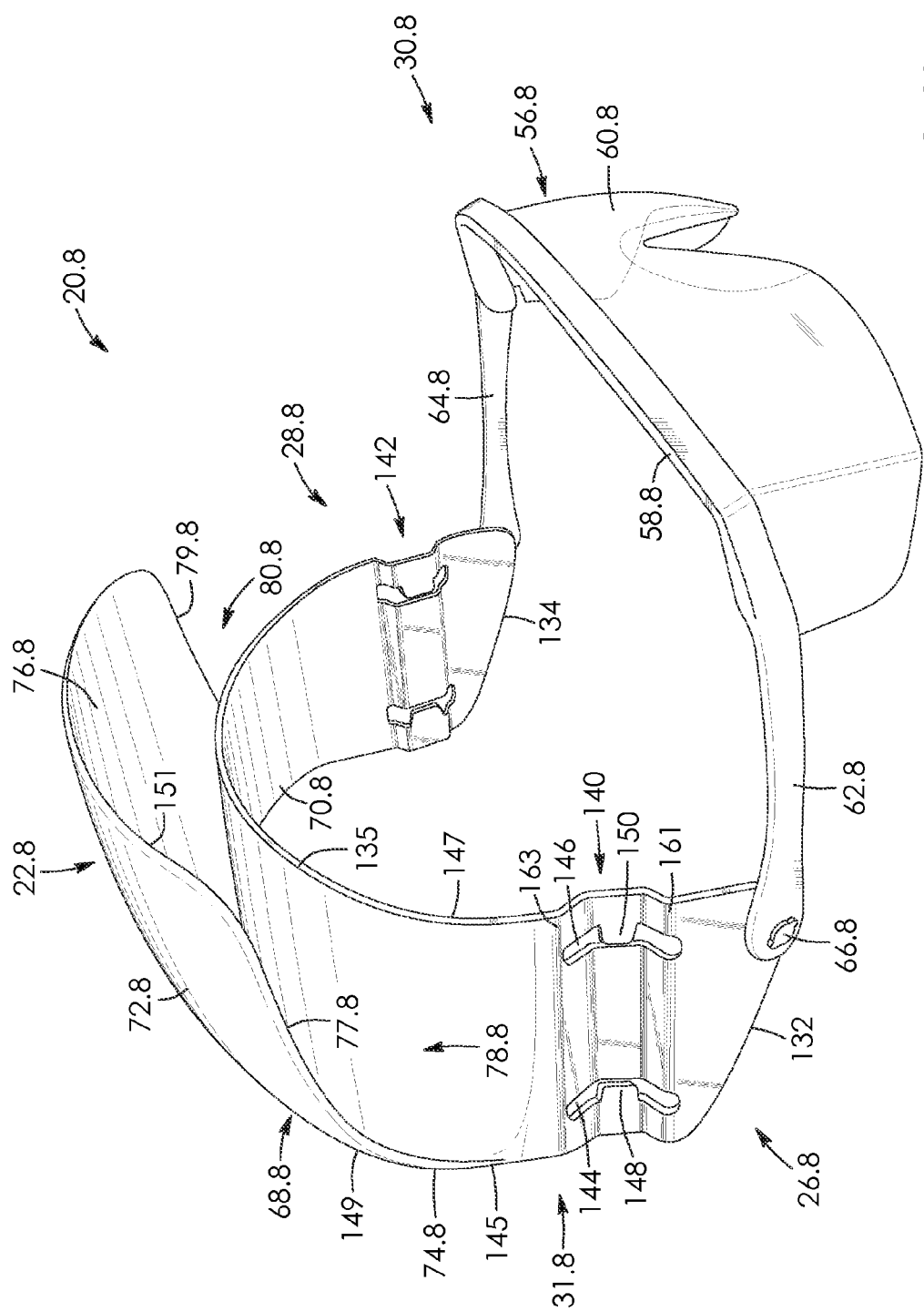
FIG. 20 is a front, side perspective view of the protective cover and eye protector of FIG. 18, with the eye protector being shown in a lowered, first position.

As seen in FIG. 18, at each end 132 and 134 of the cover 68.8 are a pair of spaced-apart ridges interposed between respective ones of the protrusions, as seen by ridges 161 and 163 by end 132 in FIG. 20, interposed between protrusion 140. The ridges and protrusions extend between the front and rear peripheral portions 147 and 149 of the cover 68.8. As seen in FIG. 21, the wires forming the headband of the ear protector 29.8 in this example abut portions of the ridges in this example in addition to the tabs, as seen by portions 165 and 167 of ridges 161 and 163 abutting wire 54.8 in addition to tab 148. In other embodiments, the headband may be formed of other material and have other shapes.

Referring to FIG. 18, each of the inwardly-extending protrusions of the protective cover has a pair of slots in this example, as seen by slots 144 and 146 for protrusion 140. The slots extend through the protrusions for selectively coupling to headband portions 52.8 and 54.8 of the ear protectors 29.8. As seen in FIG. 21, the slots are c-shaped in side profile in this example. Each of the connector mechanisms 136 comprises one of said slots 144 shaped to selectively receive therethrough a headband portion of the ear protectors. Each of the connector mechanisms 136 includes a tab in communication with its corresponding slot, with the tab being shaped to retain the headband portion of the ear protectors with the slot thereafter. This is seen by tab 148 for slot 54.8 and tab 150 for slot 52.8 in FIG. 21.

As seen in FIG. 21, the slots extend through the bottom wall 70.8 of the protective cover 68.8 in this example. The slots are elongate and extend in a direction from adjacent to the lower ends 132 of the protective cover 68.8 towards the curved upper end 135 of the bottom wall 70.8 in this example.

As seen in FIG. 21, slots 144 extend through and are positioned adjacent to rear peripheral portion 145 of the bottom wall 70.8 in this example. Slots 146 extend through and are positioned adjacent to front peripheral portion 147 of the bottom wall in this example. Tabs 148 are adjacent to the rear peripheral portion 145 of the bottom wall 70.8 and extend towards the front peripheral portion 147 thereof in this example. Tabs 150 are adjacent to the front peripheral portion 147 of the bottom wall and extend towards the rear peripheral portion 145 thereof in this example.

It will be appreciated that still more variations are possible within the scope of the invention described herein. The light apparatus shown in FIG. 6 may be connected to other parts of the assembly. For example, the lights may connect to the top or sides of frame 58.1 of the eye protector 56.1.

A further adjustment mechanism, similar to that which connects the headband to the earmuffs in FIGS. 1 to 6, may connect the eye protector to the headband. In this instance, pivoting tubes may connect to and extend from the headband and the sides of the frames of the eye protector may be partially disposed within the tubes. Alternatively, the sides of the frames of the eye protector may be in tube form and slidably engage with elongate members, such as wires, that pivotally connect to and extend from respective ends of the headband. Positioning of the eye protector relative to the wearer's face may thereby be selectively adjusted.

It will be understood by someone skilled in the art that many of the details provided above are by way of example only and are not intended to limit the scope of the invention which is to be determined with reference to at least the following claims.

What is claimed is:

1. An eye-protector assembly comprising:
    an arcuate-shaped protective cover;
    an eye-covering member pivotably connected to the protective cover, the protective cover being shaped to receive the eye-covering member when the eye-covering member is pivoted towards the cover; and
    a pair of connector mechanisms for selectively coupling the protective cover to a hearing protector, the connector mechanisms coupling to and being radially-inwardly positioned relative to the protective cover
    wherein the connector mechanisms include a pair of spaced-apart, outwardly-facing and inwardly-extending channels at lower ends of the protective cover and through each of which slots extend for selectively inserting outer portions of a headband of the hearing protector therein, and tabs adjacent to said slots for retaining the headband in place within the slots thereafter wherein the slots are through-holes in the body of the channel.

2. The assembly as claimed in claim 1 wherein the eye-covering member pivotally connects to the lower ends of the protective cover.

3. The assembly as claimed in claim 1 wherein the slots are c-shaped in side profile.

4. The assembly as claimed in claim 1 wherein the protective cover includes:
    an arcuate-shaped bottom wall having a pair spaced-apart lower ends, a curved upper end spaced-apart from and interposed between said lower ends, and a pair of spaced-apart, arcuate-shaped front and rear peripheral portions extending between said ends; and
    an arcuate-shaped top wall extending from a left side end thereof to a right side end thereof which is spaced-apart from the left side end of the top wall, the side ends of the top wall being spaced-apart above the lower ends of the bottom wall, and the top wall further including a pair of spaced-apart, arcuate-shaped front and rear peripheral portions extending between said side ends, the rear peripheral portion of the top wall operatively coupling to the rear peripheral portion of the bottom wall, the front peripheral portion of the top wall aligning with and being spaced-apart above the front peripheral portion of the bottom wall, a front opening forming thereby for receiving the eye-covering member therethrough.

5. The assembly as claimed in claim 1 wherein the protective cover includes an arcuate-shaped bottom wall, an arcuate-shaped top wall spaced-apart above the bottom wall, a closed rear at which the bottom and top walls operatively connect, and a front opening through which the eye-covering member is received when the eye-covering member is pivoted towards the protective cover, the top wall of the protective cover being angled upwards relative to the bottom wall such that the front opening of the protective cover is larger than the closed rear of the protective cover.

6. In combination, a hearing pro cc or and the eye-protector assembly as claimed in claim 1.

7. A protective cover for protecting glasses when not in use and which is connectable to a headband of a hearing protector, the headband comprising a pair of arcuate-shaped elongate members, and the protective cover including:
  spaced-apart lower ends to which frame portions of the glasses pivotally connect;
  an arcuate-shaped receptacle spaced-apart from the lower ends of the protective cover and within which lens-portions of the glasses are selectively received; and
  a pair of channels positioned adjacent to the lower ends of the cover, the channels coupling to and being radially-inwardly positioned relative to the arcuate-shaped receptacle, each of the channels including a pair of spaced-apart slots extending therethrough and a pair of tabs extending into respective ones of the slots, the arcuate-shaped elongate members of the headband of the hearing protector being received within the slots and extending tightly about the tabs wherein the slots are through-holes in the body of the channel.

8. The cover as claimed in claim 7 wherein the tabs are resilient.

9. The cover as claimed in claim 7, the cover having arcuate-shaped front and rear peripheral portions and wherein the tabs are positioned adjacent to respective ones of said peripheral portions, with the tabs positioned adjacent to the front peripheral portion extending towards the rear peripheral portion and the tabs positioned adjacent to the rear peripheral portion extending towards the front peripheral portion.

10. The cover as claimed in claim 7 the cover having arcuate-shaped front and rear peripheral portions and wherein each of the ends thereof includes a pair of spaced-apart ridges interposed between respective ones of the channels, the channels and the ridges extending between the front and rear peripheral portions and the arcuate-shaped elongate members of the headband of the hearing protector abutting portions of the ridges.

11. In combination, safety glasses and the cover as claimed in claim 7.

* * * * *

UNITED STATES PATENT AND TRADEMARK OFFICE
CERTIFICATE OF CORRECTION

PATENT NO. : 9,668,921 B2  Page 1 of 1
APPLICATION NO. : 14/702939
DATED : June 6, 2017
INVENTOR(S) : Gregg Vollet It is certified that error appears in the above-identified patent and that said Letters Patent is hereby corrected as shown below:

In the Claims

Column 10, Lines 44-64 Claim 4 should read:
4. The assembly as claimed in claim 1 wherein the protective cover includes: an arcuate-shaped bottom wall having a pair of spaced-apart lower ends, a curved upper end spaced-apart from and interposed between said lower ends, and a pair of spaced-apart, arcuate-shaped front and rear peripheral portions extending between said ends; and an arcuate-shaped top wall extending from a left side end thereof to a right side end thereof which is spaced-apart from the left side end of the top wall, the side ends of the top wall being spaced-apart above the lower ends of the bottom wall, and the top wall further including a pair of spaced-apart, arcuate-shaped front and rear peripheral portions extending between said side ends, the rear peripheral portion of the top wall operatively coupling to the rear peripheral portion of the bottom wall, the front peripheral portion of the top wall aligning with and being spaced-apart above the front peripheral portion of the bottom wall, a front opening forming thereby for receiving the eye-covering member therethrough.

Column 11, Lines 8-9 Claim 6 should read:
6. In combination, a hearing protector and the eye-protector assembly as claimed in claim 1.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*